(12) United States Patent
Ishibashi et al.

(10) Patent No.: US 10,239,841 B2
(45) Date of Patent: Mar. 26, 2019

(54) METHOD FOR PRODUCING PYRAZOLE DERIVATIVE

(71) Applicant: AGC Inc., Tokyo (JP)

(72) Inventors: Yuichiro Ishibashi, Tokyo (JP); Yosuke Ochi, Tokyo (JP); Noriaki Miyake, Tokyo (JP); Yusuke Yamazaki, Tokyo (JP); Shota Shimizu, Tokyo (JP)

(73) Assignee: AGC Inc., Tokyo (JP)

( * ) Notice: Subject to any disclaimer, the term of this patent is extended or adjusted under 35 U.S.C. 154(b) by 0 days.

(21) Appl. No.: 15/560,934

(22) PCT Filed: Mar. 23, 2016

(86) PCT No.: PCT/JP2016/059101
§ 371 (c)(1),
(2) Date: Sep. 22, 2017

(87) PCT Pub. No.: WO2016/152886
PCT Pub. Date: Sep. 29, 2016

(65) Prior Publication Data
US 2018/0079725 A1    Mar. 22, 2018

(30) Foreign Application Priority Data

Mar. 26, 2015 (JP) .................................. 2015-065271
Jun. 1, 2015 (JP) .................................. 2015-111722

(51) Int. Cl.
| | | |
|---|---|---|
| C07D 231/14 | (2006.01) | |
| C07D 231/12 | (2006.01) | |
| C07C 221/00 | (2006.01) | |
| C07C 225/14 | (2006.01) | |

(52) U.S. Cl.
CPC .......... *C07D 231/14* (2013.01); *C07C 221/00* (2013.01); *C07C 225/14* (2013.01); *C07D 231/12* (2013.01); *Y02P 20/55* (2015.11)

(58) Field of Classification Search
None
See application file for complete search history.

(56) References Cited

U.S. PATENT DOCUMENTS

| | | |
|---|---|---|
| 5,716,904 A | 2/1998 | Satow et al. |
| 5,773,388 A | 6/1998 | Satow et al. |
| 6,706,911 B1 | 3/2004 | Lui et al. |
| 2005/0221989 A1 | 10/2005 | Ehrenfreund et al. |
| 2006/0116414 A1 | 6/2006 | Dunkel et al. |
| 2006/0252944 A1 | 11/2006 | Lantzsch et al. |
| 2008/0015244 A1 | 1/2008 | Dunkel et al. |
| 2009/0197925 A1 | 8/2009 | Ehrenfreund et al. |
| 2009/0326242 A1 | 12/2009 | Pazenok et al. |
| 2010/0022782 A1 | 1/2010 | Zierke et al. |
| 2010/0204483 A1 | 8/2010 | Pazenok et al. |
| 2010/0240907 A1 | 9/2010 | Bowden et al. |
| 2010/0256390 A1 | 10/2010 | Bowden et al. |
| 2010/0292239 A1 | 11/2010 | Stierli et al. |
| 2011/0009642 A1 | 1/2011 | Pazenok |
| 2013/0023668 A1 | 1/2013 | Bowden et al. |
| 2013/0197239 A1 | 8/2013 | Pazenok et al. |
| 2013/0210809 A1* | 8/2013 | Bolea ................... C07D 417/14 514/217 |
| 2014/0107347 A1 | 4/2014 | Okamoto et al. |
| 2016/0295864 A1 | 10/2016 | Morizawa et al. |
| 2018/0194753 A1 | 7/2018 | Shao et al. |
| 2018/0273486 A1 | 9/2018 | Wang et al. |

FOREIGN PATENT DOCUMENTS

| | | |
|---|---|---|
| CN | 104496903 A | 4/2015 |
| CN | 104945325 A | 9/2015 |
| CN | 105541716 A | 5/2016 |
| JP | H08-198857 A | 8/1996 |
| JP | 2001-125224 A | 5/2001 |
| JP | 2005-511782 A | 4/2005 |
| JP | 2007-509850 A | 4/2007 |
| JP | 2010-501502 A | 1/2010 |

(Continued)

OTHER PUBLICATIONS

Ghosh et al., "Heterocyclic System II. Electrophilic Substitution on 1-Phenyl-4-(2-hydroxybenzoyl)pyrazole," *J. Indian Chem. Soc.*, 55(3): 268-271 (1978).
Hammouda et al., "1-Benzoyl-1-Phenylhydrazine as a Pyrazole Precursor," *Acta Chimica Hungarica*, 116(1): 21-27 (1984).
Okada et al., "Facile Synthetic Methods for 3- and 5-Trifluoromethyl-4-Trifluoroacetyl-Pyrazoles and their Conversion Into Pyrazole-4-Carboxylic Acids," *Heterocycles*, 34(4): 791-798 (1992).
Schmitt et al., "In Situ Generated Fluorinated Iminium Salts for Difluoromethylation and Difluoroacetylation," *Org. Lett.*, 17(18): 4510-4513 (2015).
Singh et al., "A Facile Synthesis of 5-Methyl-1-(phenyl/heterocyclyl)-4-trifluoroacetylpyrazoles," *Journal of Chemical Research (Synopses)*, 1997(4): 142-143 (1997).
Tanaka et al., "Reactions of Trifluoroacetonitrile Oxide or -nitrilimines with β-Diketones and β-Keto Esters," *Bulletin of the Chemical Society of Japan*, 59: 2631-2632 (1986).
Touzot et al., "Synthesis of trifluoromethylated pyrazoles from trifluoromethylenaminones and monosubstituted hydrazines," *Journal of Fluorine Chemistry*, 125(9): 1299-1304 (2004).

(Continued)

*Primary Examiner* — Kamal A Saeed
(74) *Attorney, Agent, or Firm* — Leydig, Voit & Mayer, Ltd.

(57) ABSTRACT

The invention relates to a production method of pyrazole derivative (6) by reacting compound (5) with an oxidant.

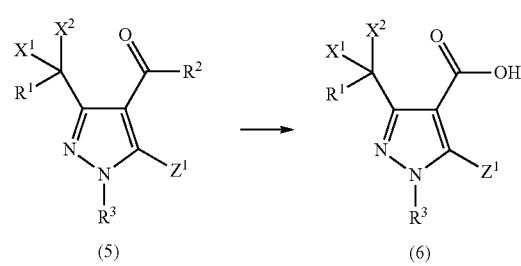

wherein $R^1$, $R^2$, $R^3$, $X^1$, $X^2$ and $Z^1$ are as defined herein.

20 Claims, No Drawings

(56) References Cited

FOREIGN PATENT DOCUMENTS

| | | |
|---|---|---|
| JP | 2010-513411 A | 4/2010 |
| JP | 2010-116334 A | 5/2010 |
| JP | 2010-531314 A | 9/2010 |
| JP | 2010-531315 A | 9/2010 |
| JP | 2010-534626 A | 11/2010 |
| JP | 2010-540477 A | 12/2010 |
| JP | 2011-518767 A | 6/2011 |
| JP | 2013-006778 A | 1/2013 |
| JP | 2013-006781 A | 1/2013 |
| KR | 2017-0017372 A | 2/2017 |
| WO | WO 1995/004725 A1 | 2/1995 |
| WO | WO 2003/070705 A1 | 8/2003 |
| WO | WO 2003/074491 A1 | 9/2003 |
| WO | WO 2009/000441 A1 | 12/2008 |
| WO | WO 2012/009009 A2 | 1/2012 |
| WO | WO 2012/176717 A1 | 12/2012 |
| WO | WO 2014/160668 A1 | 10/2014 |
| WO | WO 2015/003289 A1 | 1/2015 |
| WO | WO 2015/105129 A1 | 7/2015 |
| WO | WO 2016/152886 A1 | 9/2016 |
| WO | WO 2016/202254 A1 | 12/2016 |
| WO | WO 2017/054112 A1 | 4/2017 |
| WO | WO 2017/064550 A1 | 4/2017 |
| WO | WO 2017/129759 A1 | 8/2017 |
| WO | WO 2017/140593 A1 | 8/2017 |

OTHER PUBLICATIONS

Vasil'Ev et al., "2-(N-Alkylamino)-1-(trifluoroacetimidoyl)vinyl ketone derivatives as potential reagents in heterocyclic synthesis," *Russian Chemical Bulletin*, 57(11): 2359-2363 (2008).

Zikán et al., "Substanzen Mit Antineoplastischer Wirkung XIX. Substituterte Pyrazole Durch Reaktion Von β-4-Methoxybenzoyl-β-Chlor(Brom)Acrylsäure Mit Diazomethan," *Collection Czechoslov. Chem. Commun.*, 32(10): 3587-3596 (1967), Int'l Search Report PCT/JP2016/059101, dated Jun. 28, 2016.

Japanese Patent Office, International Search Report in International Patent Application No. PCT/JP2016/059101 dated Jun. 28, 2016.

* cited by examiner

METHOD FOR PRODUCING PYRAZOLE DERIVATIVE

CROSS-REFERENCE TO RELATED APPLICATIONS

This patent application is the U.S. national phase of International Patent Application No. PCT/JP2016/059101, filed on Mar. 23, 2016, which claims the benefit of Japanese Patent Application No. 2015-065271, filed on Mar. 26, 2015, and Japanese Patent Application No. 2015-111722, filed on Jun. 1, 2015, the disclosures of which are incorporated herein by reference in their entireties for all purposes.

TECHNICAL FIELD

The present invention relates to a novel production method of pyrazole derivatives such as pyrazolylketone derivatives, pyrazole-4-carboxylic acid derivatives and the like, which are useful as an intermediate for medicines or agrichemicals, and a novel compound useful as an intermediate for the above-mentioned production method.

BACKGROUND ART

3-Difluoromethyl-1-methyl-1H-pyrazole-4-carboxylic acid and 3-trifluoromethyl-1-methyl-1H-pyrazole-4-carboxylic acid are useful intermediates for producing pyrazolylcarboxanilide fungicides (see, for example, Patent Documents 1 and 2). As a method of producing these intermediates, multiple methods are known (see, for example, Non-Patent Document 1). As a method of converting the substituent at the 4-position on the pyrazole ring to a carboxyl group to obtain a carboxylic acid, a method of oxidizing an aldehyde to a carboxylic acid is known (see, for example, Patent Document 3).

DOCUMENT LIST

Patent Document

Patent Document 1: WO 03/070705
Patent Document 2: WO 03/074491
Patent Document 3: WO 2009/000441

Non-Patent Document

Non-Patent Document 1: Journal of Fluorine Chemistry 152 (2013) 2-11

SUMMARY OF THE INVENTION

Problems to be Solved by the Invention

The aim of the present invention is to provide a novel and industrially useful production method of a pyrazole derivative, a novel compound as an intermediate for the production method, and a production method of the novel compound.

Means of Solving the Problems

The present inventors have conducted intensive studies to solve the above-mentioned problems, and completed the present invention.

The present invention is as follows:

[1] A method of producing a pyrazole derivative represented by the following formula (6), which comprises reacting a compound represented by the following formula (5) with an oxidant;

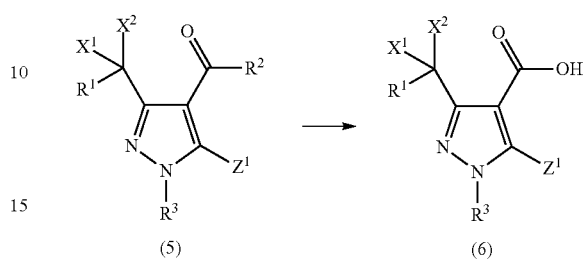

wherein
$R^1$ is a hydrogen atom, a halogen atom or a $C_{1-8}$ haloalkyl group,
$R^2$ is a $C_{1-8}$ alkyl group, a $C_{3-8}$ cycloalkyl group, a $C_{3-8}$ cycloalkyl group having substituent(s), an aryl group, an aryl group having substituent(s), a heteroaryl group or a heteroaryl group having substituent(s),
$R^3$ is a hydrogen atom, a $C_{1-8}$ alkyl group or a nitrogen-protecting group,
$X^1$ and $X^2$ are each independently a fluorine atom or a chlorine atom, and
$Z^1$ is a hydrogen atom or a $C_{1-8}$ alkyl group.

[2] A method of producing a pyrazole derivative represented by the following formula (6), which comprises reacting a compound represented by the following formula (5) with an oxidant under basic condition, and then with an acid;

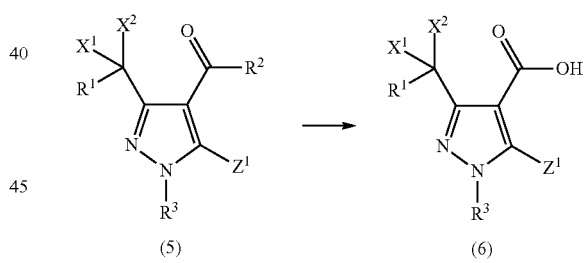

wherein
$R^1$ is a hydrogen atom, a halogen atom or a $C_{1-8}$ haloalkyl group,
$R^2$ is a $C_{1-8}$ alkyl group, a $C_{3-8}$ cycloalkyl group, a $C_{3-8}$ cycloalkyl group having substituent(s), an aryl group, an aryl group having substituent(s), a heteroaryl group or a heteroaryl group having substituent(s),
$R^3$ is a hydrogen atom, a $C_{1-8}$ alkyl group or a nitrogen-protecting group,
$X^1$ and $X^2$ are each independently a fluorine atom or a chlorine atom, and
$Z^1$ is a hydrogen atom or a $C_{1-8}$ alkyl group.

[3] A method of producing a compound represented by the following formula (6a), which comprises reacting a compound represented by the following formula (5) with an oxidant in the presence of a base;

wherein
$R^1$ is a hydrogen atom, a halogen atom or a $C_{1-8}$ haloalkyl group,
$R^2$ is a $C_{1-8}$ alkyl group, a $C_{3-8}$ cycloalkyl group, a $C_{3-8}$ cycloalkyl group having substituent(s), an aryl group, an aryl group having substituent(s), a heteroaryl group or a heteroaryl group having substituent(s),
$R^3$ is a hydrogen atom, a $C_{1-8}$ alkyl group or a nitrogen-protecting group,
$X^1$ and $X^2$ are each independently a fluorine atom or a chlorine atom,
$Z^1$ is a hydrogen atom or a $C_{1-8}$ alkyl group, and
M is a counter cation of a carboxylic acid.

[4] The method of any one of [1] to [3], wherein the substituent in $R^2$ is a group or atom inert to the reaction.

[5] The method of any one of [1] to [4], wherein the compound represented by the following formula (5) is obtained by reacting a compound represented by the following formula (3) with a compound represented by the following formula (4a) or (4b);

wherein
$R^1$, $R^2$, $R^3$, $X^1$, $X^2$ and $Z^1$ are as defined in [1],
$R^4$ is $OR^4$, $NR^5R^6$ or $SR^4$ wherein $R^4$ is a $C_{1-8}$ alkyl group, an aryl group or an aryl group having substituent(s), and $R^5$ and $R^6$ are each independently a hydrogen atom or a $C_{1-8}$ alkyl group, or $R^5$ and $R^6$ are optionally bonded to each other to form, together with the nitrogen atom to which they are bonded, a 5- to 6-membered heterocycle,
$Y^1$ is an oxygen atom or $N^+R^7R^{8+}.A^-$ wherein $R^7$ and $R^8$ are each independently a $C_{1-8}$ alkyl group, or $R^7$ and $R^8$ are optionally bonded to each other to form, together with the nitrogen atom to which they are bonded, a 5- to 6-membered heterocycle, and
$A^-$ is a counter anion,
$R^9$ and $R^{10}$ are each independently a hydrogen atom, a $C_{1-12}$ alkyl group, a $C_{1-12}$ alkyl group having substituent(s), a $C_{3-8}$ cycloalkyl group, a $C_{3-8}$ cycloalkyl group having substituent(s), an aryl group, an aryl group having substituent(s), a heteroaryl group or a heteroaryl group having substituent(s), or $R^9$ and $R^{10}$ are optionally bonded to each other to form, together with the carbon atom to which they are bonded, a 3- to 8-membered cycloalkane, a 3- to 8-membered cycloalkane having substituent(s), a 3- to 8-membered heterocycle or a 3- to 8-membered heterocycle having substituent(s), and
the wavy lines mean that the configuration of $Z^1$ and $R^A$ relating to the double bond is E or Z.

[5A] The method of [1], wherein the compound represented by the formula (5) is obtained by reacting a compound represented by the following formula (3) with a compound represented by the following formula (4a);

wherein
$R^1$, $R^2$, $R^3$, $X^1$, $X^2$ and $Z^1$ are as defined in [1],
$R^A$ is $OR^4$, $NR^5R^6$ or $SR^4$ wherein $R^4$ is a $C_{1-8}$ alkyl group, an aryl group or an aryl group having substituent(s), and $R^5$ and $R^6$ are each independently a hydrogen atom or a $C_{1-8}$ alkyl group, or $R^5$ and $R^6$ are optionally bonded to each other to form, together with the nitrogen atom to which they are bonded, a 5- to 6-membered heterocycle,
$Y^1$ is an oxygen atom or $N^+R^7R^{8+}.A^-$ wherein $R^7$ and $R^8$ are each independently a $C_{1-8}$ alkyl group, or $R^7$ and $R^8$ are optionally bonded to each other to form, together with the nitrogen atom to which they are bonded, a 5- to 6-membered heterocycle, and
$A^-$ is a counter anion, and
the wavy lines mean that the configuration of $Z^1$ and $R^A$ relating to the double bond is E or Z.

[6] The method of [5] or [5A], wherein the substituent of the $C_{1-12}$ alkyl groups having substituent(s) in $R^9$ or $R^{10}$ is each independently selected from the group consisting of —$X^A$, —$OR^B$, —$SR^B$, —$N(R^B)(R^C)$, —$Si(R^B)(R^C)(R^D)$, —CO-$OR^B$, —$(C=O)R^B$, —CN and —$CON(R^B)(R^C)$ wherein $R^B$, $R^C$ and $R^D$ are each independently a hydrogen atom or a $C_{1-8}$ alkyl group, and $X^A$ is a fluorine atom or a chlorine atom.

[7] The method of [5] or [5A], wherein the reaction of the compound represented by the formula (3) with the compound represented by the formula (4a) or (4b) is carried out in the presence of an organic base.

[8] The method of [7], wherein the organic base is a chain secondary or tertiary amine.

[9] The method of [7], wherein the organic base is dimethylamine.

[10] A method of producing a pyrazole derivative represented by the following formula (6), which comprises reacting a compound represented by the following formula (3b) with a compound represented by the following formula (4a) or (4b) to obtain a compound represented by the following formula (5), and then reacting the compound represented by the formula (5) with an oxidant;

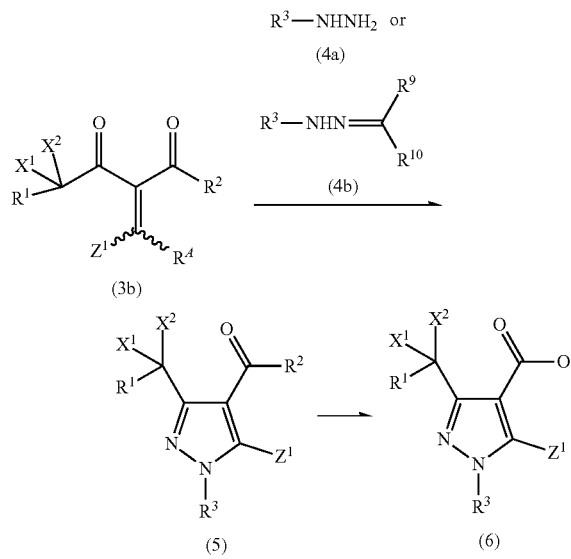

wherein
$R^1$ is a hydrogen atom, a halogen atom or a $C_{1-8}$ haloalkyl group,
$R^2$ is a $C_{1-8}$ alkyl group, a $C_{3-8}$ cycloalkyl group, a $C_{3-8}$ cycloalkyl group having substituent(s), an aryl group, an aryl group having substituent(s), a heteroaryl group or a heteroaryl group having substituent(s),
$R^3$ is a hydrogen atom, a $C_{1-8}$ alkyl group or a nitrogen-protecting group,
$X^1$ and $X^2$ are each independently a fluorine atom or a chlorine atom,
$Z^1$ is a hydrogen atom or a $C_{1-8}$ alkyl group,
$R^A$ is $OR^4$, $NR^5R^6$ or $SR^4$ wherein $R^4$ is a $C_{1-8}$ alkyl group, an aryl group or an aryl group having substituent(s), and $R^5$ and $R^6$ are each independently a hydrogen atom or a $C_{1-8}$ alkyl group, or $R^5$ and $R^6$ are optionally bonded to each other to form, together with the nitrogen atom to which they are bonded, a 5- to 6-membered heterocycle,
$R^9$ and $R^{10}$ are each independently a hydrogen atom, a $C_{1-12}$ alkyl group, a $C_{1-12}$ alkyl group having substituent(s), a $C_{3-8}$ cycloalkyl group, a $C_{3-8}$ cycloalkyl group having substituent(s), an aryl group, an aryl group having substituent(s), a heteroaryl group or a heteroaryl group having substituent(s), or $R^9$ and $R^{10}$ are optionally bonded to each other to form, together with the carbon atom to which they are bonded, a 3- to 8-membered cycloalkane, a 3- to 8-membered cycloalkane having substituent(s), a 3- to 8-membered heterocycle or a 3- to 8-membered heterocycle having substituent(s), and
the wavy lines mean that the configuration of $Z^1$ and $R^A$ relating to the double bond is E or Z.

[10A] A method of producing a pyrazole derivative represented by the following formula (6), which comprises reacting a compound represented by the following formula (3b) with a compound represented by the following formula (4a) to obtain a compound represented by the following formula (5), and then reacting the compound represented by the formula (5) with an oxidant;

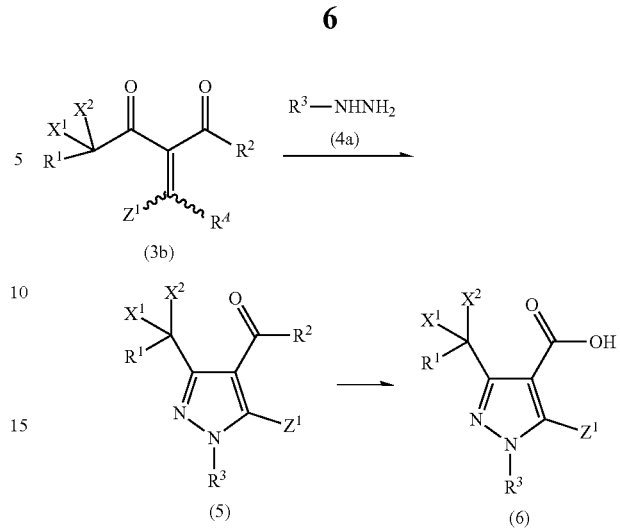

wherein
$R^1$ is a hydrogen atom, a halogen atom or a $C_{1-8}$ haloalkyl group,
$R^2$ is a $C_{1-8}$ alkyl group, a $C_{3-8}$ cycloalkyl group, a $C_{3-8}$ cycloalkyl group having substituent(s), an aryl group, an aryl group having substituent(s), a heteroaryl group or a heteroaryl group having substituent(s),
$R^3$ is a hydrogen atom, a $C_{1-8}$ alkyl group or a nitrogen-protecting group,
$X^1$ and $X^2$ are each independently a fluorine atom or a chlorine atom,
$Z^1$ is a hydrogen atom or a $C_{1-8}$ alkyl group,
$R^A$ is $OR^4$, $NR^5R^6$ or $SR^4$ wherein $R^4$ is a $C_{1-8}$ alkyl group, an aryl group or an aryl group having substituent(s), and $R^5$ and $R^6$ are each independently a hydrogen atom or a $C_{1-8}$ alkyl group, or $R^5$ and $R^6$ are optionally bonded to each other to form, together with the nitrogen atom to which they are bonded, a 5- to 6-membered heterocycle, and
the wavy lines mean that the configuration of $Z^1$ and $R^A$ relating to the double bond is E or Z.

[11] A method of producing a pyrazole derivative represented by the following formula (6), which comprises reacting a compound represented by the following formula (3b) with a compound represented by the following formula (4a) or (4b) to obtain a compound represented by the following formula (5), and then reacting the compound represented by the formula (5) with an oxidant under basic condition, and then with an acid;

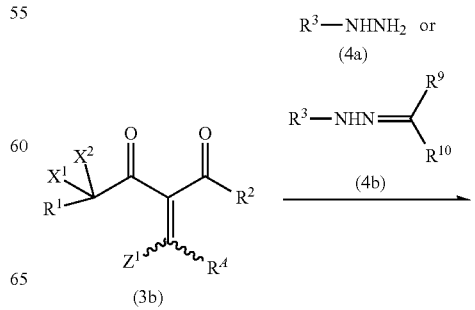

-continued

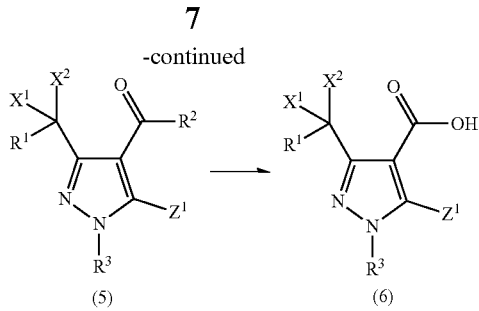

wherein
R¹ is a hydrogen atom, a halogen atom or a $C_{1-8}$ haloalkyl group,
R² is a $C_{1-8}$ alkyl group, a $C_{3-8}$ cycloalkyl group, a $C_{3-8}$ cycloalkyl group having substituent(s), an aryl group, an aryl group having substituent(s), a heteroaryl group or a heteroaryl group having substituent(s),
R³ is a hydrogen atom, a $C_{1-8}$ alkyl group or a nitrogen-protecting group,
X¹ and X² are each independently a fluorine atom or a chlorine atom,
Z¹ is a hydrogen atom or a $C_{1-8}$ alkyl group,
$R^A$ is $OR^4$, $NR^5R^6$ or $SR^4$ wherein $R^4$ is a $C_{1-8}$ alkyl group, an aryl group or an aryl group having substituent(s), and $R^5$ and $R^6$ are each independently a hydrogen atom or a $C_{1-8}$ alkyl group, or $R^5$ and $R^6$ are optionally bonded to each other to form, together with the nitrogen atom to which they are bonded, a 5- to 6-membered heterocycle,
R⁹ and R¹⁰ are each independently a hydrogen atom, a $C_{1-12}$ alkyl group, a $C_{1-12}$ alkyl group having substituent(s), a $C_{3-8}$ cycloalkyl group, a $C_{3-8}$ cycloalkyl group having substituent(s), an aryl group, an aryl group having substituent(s), a heteroaryl group or a heteroaryl group having substituent(s), or R⁹ and R¹⁰ are optionally bonded to each other to form, together with the carbon atom to which they are bonded, a 3- to 8-membered cycloalkane, a 3- to 8-membered cycloalkane having substituent(s), a 3- to 8-membered heterocycle or a 3- to 8-membered heterocycle having substituent(s), and
the wavy lines mean that the configuration of Z¹ and $R^A$ relating to the double bond is E or Z.

[12] The method of [10] or [11], wherein the substituent of the $C_{1-12}$ alkyl groups having substituent(s) in R⁹ or R¹⁰ is each independently selected from the group consisting of —$X^A$, —$OR^B$, —$SR^B$, —$N(R^B)(R^C)$, —$Si(R^B)(R^C)(R^D)$, —$COOR^B$, —$(C=O)R^B$, —CN and —$CON(R^B)(R^C)$ wherein $R^B$, $R^C$ and $R^D$ are each independently a hydrogen atom or a $C_{1-8}$ alkyl group, and $X^A$ is a fluorine atom or a chlorine atom.

[13] The method of any one of [10] to [12], wherein the compound represented by the following formula (3b) is obtained by reacting a compound represented by the following formula (3a) with water;

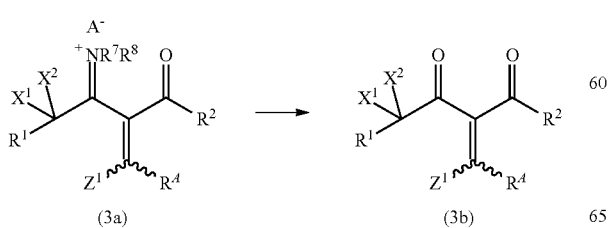

wherein
R¹, R², $R^A$, X¹, X², Z¹ and the wavy lines are as defined in [10],
R⁷ and R⁸ are each independently a $C_{1-8}$ alkyl group, or R⁷ and R⁸ are optionally bonded to each other to form, together with the nitrogen atom to which they are bonded, a 5- to 6-membered heterocycle, and
A⁻ is a counter anion.

[14] The method of [13], wherein the reaction of the compound represented by the formula (3a) with water is carried out under basic condition.

[15] The method of any one of [5] to [9], wherein the compound represented by the following formula (3) is obtained by reacting a compound represented by the following formula (1) with a compound represented by the following formula (2);

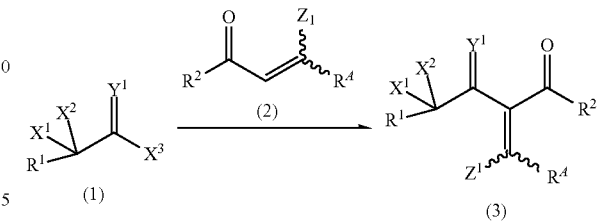

wherein
R¹, R², X¹, X² and Z¹ are as defined in [1],
$R^A$, Y¹ and the wavy lines are as defined in [5], and
X³ is a halogen atom.

[16] The method of any one of [1] to [15], wherein the oxidant is a hypochlorite.

[17] The method of any one of [1] to [16], wherein R¹ is a hydrogen atom.

[18] A method of producing a compound represented by the following formula (3a-1), which comprises reacting 1,1,2,2-tetrafluoro-N,N-dimethylethanamine with BF₃ to obtain a compound represented by the following formula (1b-1), and then reacting the compound represented by the formula (1b-1) with a compound represented by the following formula (2b-1);

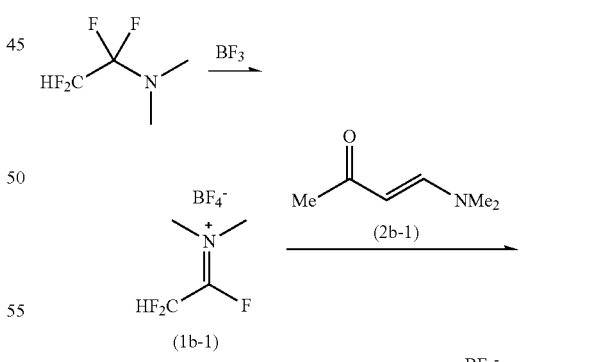

[19] A method of producing a compound represented by the following formula (5-1), which comprises reacting the compound represented by the formula (3a-1) obtained by the method of claim 18 with methylhydrazine;

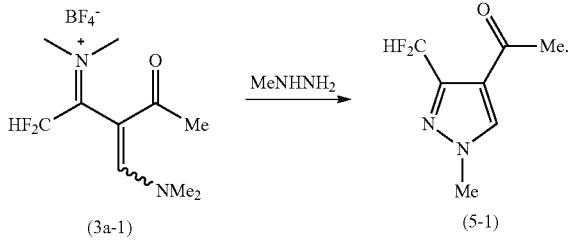

[20] A method of producing a compound represented by the following formula (5), which comprises reacting a compound represented by the following formula (3) with a compound represented by the following formula (4a) or (4b);

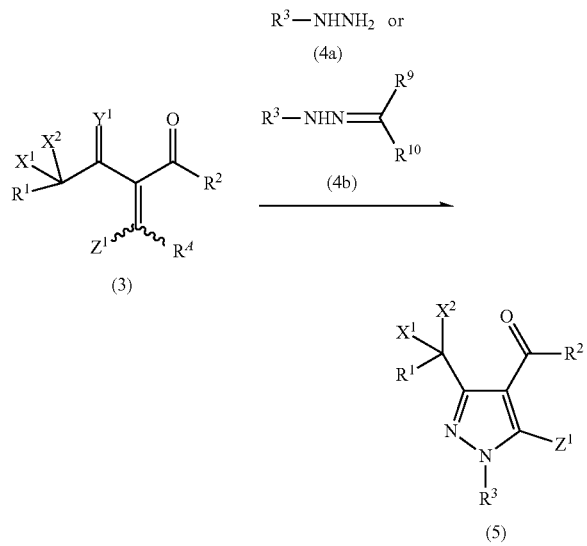

wherein
$R^1$ is a hydrogen atom, a halogen atom or a $C_{1-8}$ haloalkyl group,
$R^2$ is a $C_{1-8}$ alkyl group, a $C_{3-8}$ cycloalkyl group, a $C_{3-8}$ cycloalkyl group having substituent(s), an aryl group, an aryl group having substituent(s), a heteroaryl group or a heteroaryl group having substituent(s),
$R^3$ is a hydrogen atom, a $C_{1-8}$ alkyl group or a nitrogen-protecting group,
$X^1$ and $X^2$ are each independently a fluorine atom or a chlorine atom,
$Z^1$ is a hydrogen atom or a $C_{1-8}$ alkyl group,
$R^4$ is $OR^4$, $NR^5R^6$ or $SR^4$ wherein $R^4$ is a $C_{1-8}$ alkyl group, an aryl group or an aryl group having substituent(s), and $R^5$ and $R^6$ are each independently a hydrogen atom or a $C_{1-8}$ alkyl group, or $R^5$ and $R^6$ are optionally bonded to each other to form, together with the nitrogen atom to which they are bonded, a 5- to 6-membered heterocycle,
$Y^1$ is an oxygen atom or $N^+R^7R^8 \cdot A^-$ wherein $R^7$ and $R^8$ are each independently a $C_{1-8}$ alkyl group, or $R^7$ and $R^8$ are optionally bonded to each other to form, together with the nitrogen atom to which they are bonded, a 5- to 6-membered heterocycle, and $A^-$ is a counter anion,
$R^9$ and $R^{10}$ are each independently a hydrogen atom, a $C_{1-12}$ alkyl group, a $C_{1-12}$ alkyl group having substituent(s), a $C_{3-8}$ cycloalkyl group, a $C_{3-8}$ cycloalkyl group having substituent(s), an aryl group, an aryl group having substituent(s), a heteroaryl group or a heteroaryl group having substituent(s), or $R^9$ and $R^{10}$ are optionally bonded to each other to form, together with the carbon atom to which they are bonded, a 3- to 8-membered cycloalkane, a 3- to 8-membered cycloalkane having substituent(s), a 3- to 8-membered heterocycle or a 3- to 8-membered heterocycle having substituent(s), and
the wavy lines mean that the configuration of $Z^1$ and $R^4$ relating to the double bond is E or Z.

[21] A method of producing a compound represented by the following formula (3b), which comprises reacting a compound represented by the following formula (3a) with water;

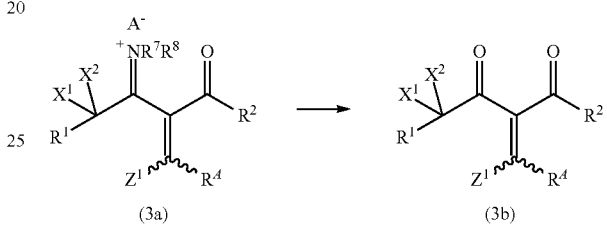

wherein
$R^1$ is a hydrogen atom, a halogen atom or a CL-s haloalkyl group,
$R^2$ is a $C_{1-8}$ alkyl group, a $C_{3-8}$ cycloalkyl group, a $C_{3-8}$ cycloalkyl group having substituent(s), an aryl group, an aryl group having substituent(s), a heteroaryl group or a heteroaryl group having substituent(s),
$X^1$ and $X^2$ are each independently a fluorine atom or a chlorine atom,
$Z^1$ is a hydrogen atom or a $C_{1-8}$ alkyl group,
$R^4$ is $OR^4$, $NR^5R^6$ or $SR^4$ wherein $R^4$ is a $C_{1-8}$ alkyl group, an aryl group or an aryl group having substituent(s), and $R^5$ and $R^6$ are each independently a hydrogen atom or a $C_{1-8}$ alkyl group, or $R^5$ and $R^6$ are optionally bonded to each other to form, together with the nitrogen atom to which they are bonded, a 5- to 6-membered heterocycle,
$R^7$ and $R^8$ are each independently a $C_{1-8}$ alkyl group, or $R^7$ and $R^8$ are optionally bonded to each other to form, together with the nitrogen atom to which they are bonded, a 5- to 6-membered heterocycle,
$A^-$ is a counter anion, and
the wavy lines mean that the configuration of $Z^1$ and $R^4$ relating to the double bond is E or Z.

[22] A method of producing a compound represented by the following formula (3), which comprises reacting a compound represented by the following formula (1) with a compound represented by the following formula (2);

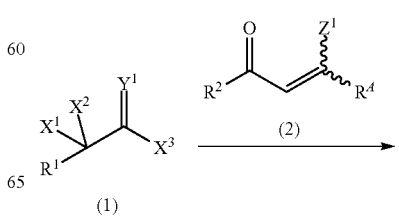

-continued

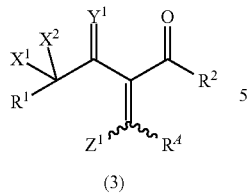

(3)

wherein
$R^1$ is a hydrogen atom, a halogen atom or a $C_{1-8}$ haloalkyl group,
$R^2$ is a $C_{1-8}$ alkyl group, a $C_{3-8}$ cycloalkyl group, a $C_{3-8}$ cycloalkyl group having substituent(s), an aryl group, an aryl group having substituent(s), a heteroaryl group or a heteroaryl group having substituent(s),
$X^1$ and $X^2$ are each independently a fluorine atom or a chlorine atom,
$Z^1$ is a hydrogen atom or a $C_{1-8}$ alkyl group,
$R^4$ is $OR^4$, $NR^5R^6$ or $SR^4$ wherein $R^4$ is a $C_{1-8}$ alkyl group, an aryl group or an aryl group having substituent(s), and $R^5$ and $R^6$ are each independently a hydrogen atom or a $C_{1-8}$ alkyl group, or $R^5$ and $R^6$ are optionally bonded to each other to form, together with the nitrogen atom to which they are bonded, a 5- to 6-membered heterocycle,
$Y^1$ is an oxygen atom or $N^+R^7R^8.A^-$ wherein $R^7$ and $R^8$ are each independently a $C_{1-8}$ alkyl group, or $R^7$ and $R^8$ are optionally bonded to each other to form, together with the nitrogen atom to which they are bonded, a 5- to 6-membered heterocycle, and
$A^-$ is a counter anion,
$X^3$ is a halogen atom, and
the wavy lines mean that the configuration of $Z^1$ and $R^4$ relating to the double bond is E or Z.

[23] A compound represented by the following formula (5a);

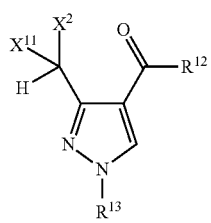

(5a)

wherein
$R^{12}$ is a $C_{1-8}$ alkyl group,
$R^{13}$ is a hydrogen atom, a $C_{1-8}$ alkyl group or a nitrogen-protecting group, and
$X^{11}$ and $X^{12}$ are each independently a fluorine atom or a chlorine atom,
provided that a compound wherein $R^{12}$ is a methyl group, $R^{13}$ is a nitrogen-protecting group, and $X^{11}$ and $X^{12}$ are both fluorine atoms is excluded.

[24] The compound of [23], wherein $R^{12}$ is a methyl group or an ethyl group, $R^{13}$ is a hydrogen atom, a methyl group or an ethyl group, and $X^{11}$ and $X^{12}$ are both fluorine atoms.

[25] A compound represented by the following formula (3c);

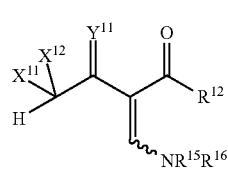

(3c)

wherein
$R^{12}$ is a $C_{1-8}$ alkyl group,
$R^{15}$ and $R^{16}$ are each independently a hydrogen atom or a $C_{1-8}$ alkyl group, or $R^{15}$ and $R^{16}$ are optionally bonded to each other to form, together with the nitrogen atom to which they are bonded, a 5- to 6-membered heterocycle,
$X^{11}$ and $X^{12}$ are each independently a fluorine atom or a chlorine atom,
$Y^{11}$ is an oxygen atom or $N^+R^{17}R^{18}.A^-$ wherein $R^{17}$ and $R^{18}$ are each independently a $C_{1-8}$ alkyl group, or $R^{17}$ and $R^{18}$ are optionally bonded to each other to form, together with the nitrogen atom to which they are bonded, a 5- to 6-membered heterocycle, and
$A^-$ is a counter anion, and
the wavy line means that the configuration of $NR^{15}R^{16}$ relating to the double bond is E or Z.

[26] A compound represented by the following formula (3d);

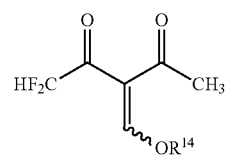

(3d)

wherein
$R^{14}$ is a $C_{1-2}$ alkyl group, and
the wavy line means that the configuration of $OR^{14}$ relating to the double bond is E or Z.

Effect of the Invention

According to the production method of the present invention, pyrazole derivatives useful as intermediates for medicines or agrichemicals can be produced by an industrially advantageous and economically excellent method. That is to say, the substrates and reaction materials used in the production method of the present invention are selected from materials with easy handling and availability, and neither special reactor or special reaction condition is used in each reaction, and therefore, the production method of the present invention is suitable as an industrial production method. In addition, since the reaction in the production method of the present invention proceeds regioselectively on the two nitrogen atoms of the pyrazole ring, the objective derivative can be produced with high selectivity in a high-yield. Therefore, the production method of the present invention employing the reaction is an economically excellent method.

Moreover, the present invention provides a novel intermediate used in the production method.

DESCRIPTION OF EMBODIMENTS

The embodiments of the present invention are explained below in detail.

Definition of Term

In the present specification, numerical range shown by using "to" means the range including the numerical values described before and after "to" as minimum and maximum values.

C1 means that the number of the carbon atom is 1, and the other expressions are the same in meaning.

In the present specification, the "$C_{1-8}$ alkyl group" means a linear or branched alkyl group having 1 to 8 carbon atoms, and examples thereof include a methyl group, an ethyl group, a propyl group, an isopropyl group, a butyl group, an isobutyl group, a s-butyl group, a t-butyl group, a pentyl group, a hexyl group, a heptyl group, an octyl group and the like.

In the present specification, "$C_{1-12}$ alkyl group" means a linear or branched alkyl group having 1 to 12 carbon atoms, and examples thereof include a methyl group, an ethyl group, a propyl group, an isopropyl group, a butyl group, an isobutyl group, a s-butyl group, a t-butyl group, a pentyl group, a hexyl group, a heptyl group, an octyl group, a nonyl group, a decyl group, an undecyl group, a dodecyl group and the like.

The "$C_{1-8}$ haloalkyl group" means a group wherein the one or more hydrogen atoms of the above-mentioned alkyl group are replaced with halogen atoms. Examples of the halogen atom include a bromine atom, an iodine atom, a fluorine atom and a chlorine atom. Examples of the $C_{1-8}$ haloalkyl group include a bromomethyl group, a 2-bromoethyl group, a 3-bromopropyl group, a 4-bromobutyl group, a 5-bromopentyl group, a 6-bromohexyl group, an iodomethyl group, a 2-iodoethyl group, a 3-iodopropyl group, a 4-iodobutyl group, a 5-iodopentyl group, a 6-iodohexyl group, a fluoromethyl group, a 2-fluoroethyl group, a 3-fluoropropyl group, a 4-fluorobutyl group, a 5-fluoropentyl group, a 6-fluorohexyl group, a tribromomethyl group, a trichloromethyl group, a trifluoromethyl group and the like.

The "$C_{3-8}$ cycloalkyl group" means a cycloalkyl group having 3 to 8 carbon atoms, and examples thereof include a cyclopropyl group, a cyclobutyl group, a cyclopentyl group, a cyclohexyl group, a cyclooctyl group and the like.

The "substituent" is a known substituent, and selected from substituents that do not affect the reaction in the production method of the present invention.

The "$C_{3-8}$ cycloalkyl group having substituent(s)" means a group wherein the one or more hydrogen atoms of the above-mentioned cycloalkyl group are replaced with substituents. The substituent is selected from substituents that do not affect the reaction in the production method of the present invention, and examples thereof include a $C_{1-8}$ alkyl group, a $C_{1-8}$ alkoxy group, an aryl group and the like. The number of the carbon atom of the $C_{3-8}$ cycloalkyl group having substituent(s) is 3 to 8 including the number of the carbon atom of the substituent(s). Examples of the $C_{3-8}$ cycloalkyl group having substituent(s) include a 2-methylcyclopropyl group, a 1-methylcyclopentyl group, a 4-methylcyclohexyl group and the like.

The "$C_{1-8}$ alkoxy group" means a group RO— wherein R is a $C_{1-8}$ alkyl group, and examples thereof include a methoxy group, an ethoxy group, a propyloxy group, an isopropyloxy group, a butoxy group, an isobutyloxy group, a s-butyloxy group, a t-butyloxy group, a hexyloxy group and the like.

The "$C_{3-8}$ cycloalkoxy group" means a group RO— wherein R is a $C_{3-8}$ cycloalkyl group, and examples thereof include a cyclopropyloxy group, a cyclobutyloxy group, a cyclopentyloxy group, a cyclohexyloxy group and the like.

The "aryl group" means an aromatic hydrocarbon group having 6 to 18 carbon atoms, and examples thereof include a phenyl group, a naphthyl group, an anthryl group and the like.

The "aryl group having substituent(s)" means a group wherein the one or more hydrogen atoms of the above-mentioned aryl group are replaced with substituents. The substituent is selected from substituents that do not affect the reaction in the production method of the present invention, and examples thereof include a $C_{1-8}$ alkyl group, a $C_{1-8}$ alkoxy group, a $C_{3-8}$ cycloalkyl group, a $C_{3-8}$ cycloalkoxy group, a halogen atom and the like. Examples of the aryl group having substituent(s) include a 2-methylphenyl group (an o-tolyl group), a 3-methylphenyl group (a m-tolyl group), a 4-methylphenyl group (a p-tolyl group), a 2,4-di-t-butylphenyl group, a 4-methoxyphenyl group, a 4-chlorophenyl group and the like.

The "heteroaryl group" means a monovalent 3- to 10-membered aromatic heterocyclic group containing at least one hetero atom selected from a nitrogen atom, an oxygen atom and a sulfur atom, and examples thereof include furyl, benzofuranyl, dibenzofuranyl, thienyl, benzothienyl, dibenzothienyl, pyrrolyl, indolyl, carbazolyl, imidazolyl, benzimidazolyl, pyrazolyl, oxazolyl, benzoxazolyl, thiazolyl, benzothiazolyl, furazanyl, pyridyl, pyranyl, pyrazinyl, pyrimidinyl, pyridazinyl, triazinyl, quinolyl, indolizinyl, cinnolinyl, purinyl, carbolinyl, phenanthrolinyl, imidazopyrimidinyl and the like.

The "heteroaryl group having substituent(s)" means a group wherein the one or more hydrogen atoms of the above-mentioned heteroaryl group are replaced with substituents. The substituent is selected from substituents that do not affect the reaction in the production method of the present invention, and examples thereof include a $C_{1-8}$ alkyl group, a $C_{1-8}$ alkoxy group, a $C_{3-8}$ cycloalkyl group, a $C_{3-8}$ cycloalkoxy group, a halogen atom, an aryl group and the like.

The substituent of the "$C_{1-12}$ alkyl group having substituent(s)" is selected from substituents that do not affect the reaction in the production method of the present invention, and examples thereof include groups selected from the group consisting of —$X^A$, —$OR^B$, —$SR^B$, —$N(R^B)(R^C)$, —$Si(R^B)(R^C)(R^D)$, —$COOR^B$, —$(C=O)R^B$, —CN and —$CON(R^B)(R^C)$ wherein $R^B$, $R^C$ and $R^D$ are each independently a hydrogen atom or a $C_{1-8}$ alkyl group, and $X^A$ is a fluorine atom or a chlorine atom.

The "5- to 6-membered heterocycle" optionally formed by $R^5$ and $R^6$ or $R^7$ and $R^8$ bonded to each other, together with the nitrogen atom to which they are bonded, means a 5- to 6-membered monovalent saturated or unsaturated heterocycle containing at least one nitrogen atom, and optionally containing at least one additional hetero atom selected from a nitrogen atom, an oxygen atom and a sulfur atom, and examples of the 5- to 6-membered heterocycle include pyrrole, pyrroline, pyrrolidine, imidazole, imidazoline, imidazolidine, pyrazole, pyrazoline, pyrazolidine, pyridine, piperidine, pyrazine, piperazine, pyrimidine, pyridazine, thiazole, thiazoline, thiazolidine, isothiazole, isothiazoline, isothiazolidine, oxazole, oxazoline, oxazolidine, isoxazole, isoxazoline, isoxazolidine, morpholine and the like.

The "$C_{3-8}$ cycloalkane" optionally formed by $R^9$ and $R^{10}$ bonded to each other, together with the carbon atom to which they are bonded, means a cycloalkane having 3 to 8 carbon atoms, and examples thereof include cyclopropane, cyclobutane, cyclopentane, cyclohexane, cyclooctane and the like.

The "C$_{3-8}$ cycloalkane having substituent(s)" optionally formed by R$^9$ and R$^{10}$ bonded to each other, together with the carbon atom to which they are bonded, means a group wherein the one or more hydrogen atoms of the above-mentioned cycloalkane are replaced with substituents. The substituent is selected from substituents that do not affect the reaction in the production method of the present invention, and examples thereof include a C$_{1-8}$ alkyl group, a C$_{1-8}$ alkoxy group, an aryl group and the like. The number of the carbon atom of the C$_{3-8}$ cycloalkane having substituent(s) is 3 to 8 including the number of the carbon atom of the substituent(s). Examples of the C$_{3-8}$ cycloalkane having substituent(s) include 2-methylcyclopropane, 1-methylcyclopentane, 4-methylcyclohexane and the like.

The "3- to 8-membered heterocycle" optionally formed by R$^9$ and R$^{10}$ bonded to each other, together with the carbon atom to which they are bonded, means a 3- to 8-membered monovalent saturated or unsaturated heterocycle containing at least one nitrogen atom, and optionally containing at least one additional hetero atom selected from a nitrogen atom, an oxygen atom and a sulfur atom, and examples of the 3- to 8-membered heterocycle include aziridine, azetidine, pyrrole, pyrroline, pyrrolidine, imidazole, imidazoline, imidazolidine, pyrazole, pyrazoline, pyrazolidine, pyridine, piperidine, pyrazine, piperazine, pyrimidine, pyridazine, thiazole, thiazoline, thiazolidine, isothiazole, isothiazoline, isothiazolidine, oxazole, oxazoline, oxazolidine, isoxazole, isoxazoline, isoxazolidine, morpholine, azepane, azepine and the like.

The "3- to 8-membered heterocycle having substituent(s)" optionally formed by R$^9$ and R$^{10}$ bonded to each other, together with the carbon atom to which they are bonded, means a group wherein the one or more hydrogen atoms of the above-mentioned 3- to 8-membered heterocycle are replaced with substituents. The substituent is selected from substituents that do not affect the reaction in the production method of the present invention, and examples thereof include a C$_{1-8}$ alkyl group, a C$_{1-8}$ alkoxy group, a C$_{3-8}$ cycloalkyl group, a C$_{3-8}$ cycloalkoxy group, a halogen atom, an aryl group and the like.

The "halogen atom" means an iodine atom, a bromine atom, a chlorine atom or a fluorine atom.

The "nitrogen-protecting group" means a protecting group which is not eliminated in each reaction in the production method of the present invention, and is eliminated by other chemical methods (e.g., chemical methods generally used in organic synthetic chemistry, such as hydrogenation, hydrolysis, electrolysis, photolysis) to give N—H. Such protecting group is selected from protecting groups which is publicly or commonly known which is known generally as a protecting group for an amino group. Examples thereof include alkylcarbamate-type protecting groups such as a t-butyldiphenylsilyl group, a t-butyldimethylsilyl group, a methoxycarbonyl group, an ethoxycarbonyl group, a t-butoxycarbonyl (Boc) group and the like; arylalkylcarbamate-type protecting groups such as a 9-fluorenylmethyloxycarbonyl (Fmoc) group and the like; arylsulfonamide-type protecting groups such as a benzenesulfonyl group, a p-toluenesulfonyl (Ts) group and the like; and amide-type protecting groups such as a formamido group, an acetamido group, a trifluoroacetamido (TFA) group and the like, which are publicly known to those skilled in the art from reference books in organic synthetic chemistry, such as "Protective Groups in Organic Synthesis" (T. W. Greene et. al, John Wiley & Sons, inc.) and the like.

The "counter anion" is preferably an anion selected from the group consisting of halide ions, fluorohydrogenate anions ((HF)$_n$F$^-$, wherein n is an integer), halogen oxoacid ions, inorganic acid ions and organic acid ions. Examples of the halide ion include a fluoride ion (F$^-$), a chloride ion (Cl$^-$), a bromide ion (Br$^-$) and an iodide ion (I$^-$). Examples of the halogen oxoacid ion include a hypochlorite ion (ClO$^-$), a chlorite ion (ClO$_2^-$), a chlorate ion (ClO$_3^-$), a perchlorate ion (ClO$_4^-$), a hypobromite ion (BrO$^-$), a bromite ion (BrO$_2^-$), a bromate ion (BrO$_3^-$), a bromate ion (BrO$_4^-$), a hypoiodite ion (IO$^-$), an iodite ion (IO$_2^-$), an iodate ion (IO$_3^-$), a periodate ion (IO$_4^-$) and the like. Examples of the inorganic acid ion include a hydroxide ion, a carbonate ion, a hydrogencarbonate ion, a sulfate ion, a hydrogensulfate ion, a phosphate ion, a hydrogenphosphate ion, a dihydrogenphosphate ion, a nitrate ion, a borate ion, a tetrafluoroborate ion and the like. Examples of the organic acid ion include an acetate ion, a trifluoroacetate ion, a trifluoromethanesulfonate ion, a tetraphenylborate ion and the like.

Examples of the "counter cation" include Na$^+$, K$^+$, ½Ca$^{2+}$, NH$_4^+$ and the like.

[Production Route of the Present Invention]

The summary of the production route of the present invention is shown in the following Scheme 1. The embodiment of the present invention is explained in detail with respect to each step of Scheme 1. In the embodiment of the present invention, each step may be independently performed, and some or all steps may be continuously performed. When multiple steps are continuously performed, after stopping the reaction in each step or not, the next step may be performed. In addition, the next step may be performed with or without purification after the completion of the step. The stop of the reaction and purification are optional. The reactions in multiple steps may be performed in the same reaction container or different reaction container. "Compound (n)" means the compound represented by the formula (n).

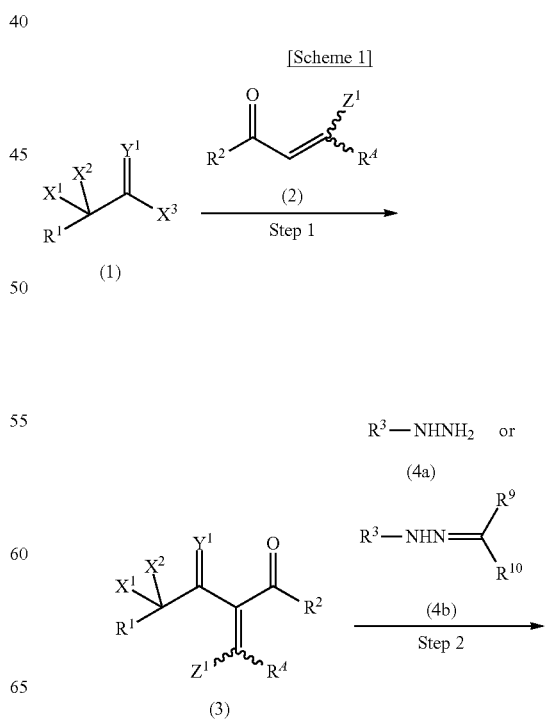

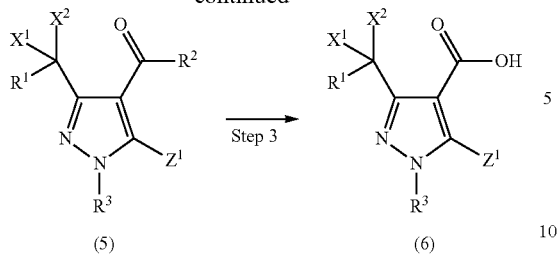

(5) → (6)

$R^1$ is a hydrogen atom, a halogen atom or a $C_{1-8}$ haloalkyl group.

$R^2$ is a $C_{1-8}$ alkyl group, a $C_{3-8}$ cycloalkyl group, a $C_{3-8}$ cycloalkyl group having substituent(s), an aryl group, an aryl group having substituent(s), a heteroaryl group or a heteroaryl group having substituent(s).

$R^3$ is a hydrogen atom, a $C_{1-8}$ alkyl group or a nitrogen-protecting group.

$R^4$ is $OR^4$, $NR^5R^6$ or $SR^4$ wherein $R^4$ is a $C_{1-8}$ alkyl group, an aryl group or an aryl group having substituent(s), and $R^5$ and $R^6$ are each independently a hydrogen atom or a $C_{1-8}$ alkyl group, or $R^5$ and $R^6$ are optionally bonded to each other to form, together with the nitrogen atom to which they are bonded, a 5- to 6-membered heterocycle.

$X^1$ and $X^2$ are each independently a fluorine atom or a chlorine atom.

$Z^1$ is a hydrogen atom or a $C_{1-8}$ alkyl group.

$Y^1$ is an oxygen atom or $N^+R^7R^8.A^-$ wherein $R^7$ and $R^8$ are each independently a $C_{1-8}$ alkyl group, or $R^7$ and $R^8$ are optionally bonded to each other to form, together with the nitrogen atom to which they are bonded, a 5- to 6-membered heterocycle, and $A^-$ is a counter anion.

$R^9$ and $R^{10}$ are each independently a hydrogen atom, a $C_{1-12}$ alkyl group, a $C_{1-12}$ alkyl group having substituent(s), a $C_{3-8}$ cycloalkyl group, a $C_{3-8}$ cycloalkyl group having substituent(s), an aryl group, an aryl group having substituent(s), a heteroaryl group or a heteroaryl group having substituent(s), or $R^9$ and $R^{10}$ are optionally bonded to each other to form, together with the carbon atom to which they are bonded, a 3- to 8-membered cycloalkane, a 3- to 8-membered cycloalkane having substituent(s), a 3- to 8-membered heterocycle or a 3- to 8-membered heterocycle having substituent(s).

$X^3$ is a halogen atom.

The wavy lines in the formula (2) and (3) mean that the configuration of $Z^1$ and $R^4$ relating to the double bond is E or Z.

[Production Step: Compound (1)→Compound (3) (Step 1)]

Compound (3) can be produced by reacting compound (1) with compound (2). Hereinafter, the step of producing compound (3) from compound (1) is referred to as Step 1.

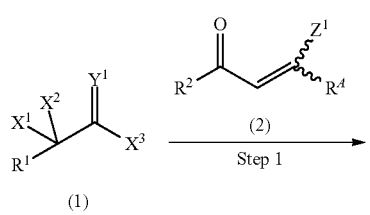

(1)

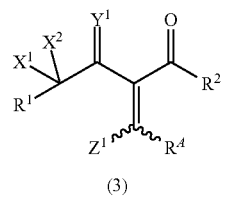

(3)

In compound (1), $X^1$ and $X^2$ are each independently a fluorine atom or a chlorine atom, preferably a fluorine atom.

$X^3$ is a halogen atom, preferably a fluorine atom or a chlorine atom.

$R^1$ is a hydrogen atom, a halogen atom or a $C_{1-8}$ haloalkyl group, preferably a hydrogen atom or a halogen atom, more preferably a hydrogen atom or a fluorine atom, most preferably a hydrogen atom.

Compound (1) wherein $R^1$ is a hydrogen atom, and $X^1$ and $X^2$ are both fluorine atoms is most preferable.

$Y^1$ is an oxygen atom or $N^+R^7R^8.A^-$ Compound (1) wherein $Y^1$ is an oxygen atom is a compound represented by the following formula (1a). Compound (1) wherein $Y^1$ is $N^+R^7R^8.A^-$ is a compound represented by the following formula (1b).

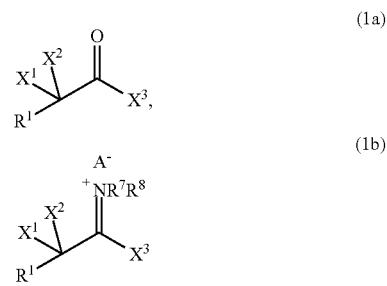

$R^7$ and $R^8$ are each independently a $C_{1-8}$ alkyl group, or $R^7$ and $R^8$ are optionally bonded to each other to form, together with the nitrogen atom to which they are bonded, a 5- to 6-membered heterocycle. $R^7$ and $R^8$ are preferably each independently a methyl group or an ethyl group, or $R^7$ and $R^8$ are preferably bonded to each other to form, together with the nitrogen atom to which they are bonded, pyrrolidine, piperidine or morpholine.

$A^-$ is a counter anion, preferably a halide ion such as a fluoride ion, a chloride ion and the like or a tetrafluoroborate ion ($BF_4^-$).

Compound (1a), which is compound (1) wherein $Y^1$ is an oxygen atom, is commercially available, and, for example, 2,2-difluoroacetic chloride is easily available as a commercial product. Alternatively, compound (1a) can be produced from the corresponding carboxylic acid ($CR^1X^1X^2COOH$), which is a commercial product, according to a known method (e.g., Journal of Fluorine Chemistry 23 (1983) 383-388, Japanese Patent No. 3632243).

Compound (1b), which is compound (1) wherein $Y^1$ is $N^+R^7R^8.A^-$, can be produced from the corresponding amine ($CR^1X^1X^2CX^3_2NR^7R^8$) and acid (the acid is a counter anion ($A^-$) source), which are commercial products, according to a known method (e.g., WO 2008/022777).

When compound (1) is produced according to a known method, compound (1) after post-treatment may be used as a raw material compound in Step 1. In addition, compound (1) may be subjected to the subsequent purification for higher purity. When compound (1) is likely to be decomposed by water, air, heat and the like, compound (1) is preferably used in the reaction of Step 1 without purification.

Compound (1) is preferably compound (1a), which is compound (1) wherein $Y^1$ is an oxygen atom, because it can be available at a lower price or produced in shorter steps.

In compound (2), $Z^1$ is a hydrogen atom or a $C_{3-8}$ alkyl group, preferably a hydrogen atom or a methyl group.

$R^2$ is a $C_{1-8}$ alkyl group, a $C_{3-8}$ cycloalkyl group, a $C_{3-8}$ cycloalkyl group having substituent(s), an aryl group, an aryl group having substituent(s), a heteroaryl group or a heteroaryl group having substituent(s), preferably a $C_{1-8}$ alkyl group, a $C_{3-8}$ cycloalkyl group, an aryl group or a heteroaryl group, more preferably a $C_{1-8}$ alkyl group, further more preferably a methyl group or an ethyl group, still more preferably a methyl group.

$R^A$ is $OR^4$, $NR^5R^6$ or $SR^4$. Compound (2) wherein $R^A$ is $OR^4$ is a compound represented by the following formula (2a). Compound (2) wherein $R^A$ is $NR^5R^6$ is a compound represented by the following formula (2b).

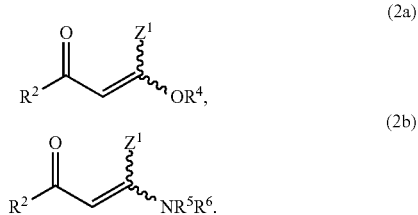

$R^4$ is a $C_{1-8}$ alkyl group, an aryl group or an aryl group having substituent(s), preferably a $C_{1-8}$ alkyl group or an aryl group, more preferably a methyl group, an ethyl group or a phenyl group.

$R^5$ and $R^6$ are each independently a hydrogen atom or a $C_{1-8}$ alkyl group, or $R^5$ and $R^6$ are optionally bonded to each other to form, together with the nitrogen atom to which they are bonded, a 5- to 6-membered heterocycle. $R^5$ and $R^6$ are preferably each independently a hydrogen atom, a methyl group or an ethyl group, or $R^5$ and $R^6$ are preferably bonded to each other to form, together with the nitrogen atom to which they are bonded, pyrrolidine, piperidine or morpholine.

The wavy lines mean that the configuration of $Z^1$ and $R^A$ relating to the double bond is E or Z. E/Z may be changed before or after the reaction of Step 1.

Compound (2) is commercially available, and, for example, 4-methoxy-3-buten-2-one (example of compound (2a)) and 1-(dimethylamino)-1-buten-3-one (example of compound (2b)) are easily available as a commercial product. Alternatively, it can be produced from a commercial reagent according to a known method. For example, compound (2a) can be produced according to the method described in US 20080287421 A1, and compound (2b) can be produced according to the method described in CN 101781222 A. When compound (2) is produced according to a known method, compound (2) after post-treatment may be used as a raw material compound in Step (2). In addition, compound (1) may be subjected to the subsequent purification for higher purity.

In Step 1, the addition order of compound (1) and compound (2) is not particularly limited. While the amount of compound (2) to be used is not particularly limited, it is preferably 0.8 to 3.0 mol, more preferably 0.9 to 2.0 mol, further more preferably 0.9 to 1.8 mol, per 1 mol of compound (1), from the aspect of economy.

Since an acidic by-product is generated in the reaction of compound (1) with compound (2), the reaction may be performed in the presence of a base as an acid scavenger. Examples of the base include metal hydrides such as sodium hydride, potassium hydride, calcium hydride and the like; organic amines such as imidazole, pyridine, 2,6-lutidine, s-collidine, N-methylpyrrolidine, N-methylpiperidine, tri ($C_{1-4}$ alkyl)amines including ethyldiisopropylamine, triethylamine and tributylamine, and the like; inorganic salts such as sodium hydroxide, potassium hydroxide, potassium carbonate, sodium hydrogencarbonate, sodium fluoride, potassium fluoride and the like, and the like. From the aspect of yield improvement, preferred are organic amines, and more preferred are pyridine and triethylamine.

The amount of the base to be used is preferably 0.3 to 4.0 mol, more preferably 0.3 to 2.0 mol, further more preferably 0.5 to 1.5 mol, per 1 mol of compound (1). When compound (1) contains an acidic impurity (impurity in the production of compound (1), etc.), the amount of the base to be used is preferably increased. In this case, the amount of the base to be used is preferably 0.3 to 5.0 mol, more preferably 0.3 to 3.0 mol, further more preferably 0.5 to 1.5 mol, per 1 mol of compound (1).

The reaction of compound (1) with compound (2) may be performed in the presence of a solvent. The solvent is preferably selected from solvents inert to the reaction, and is appropriately selected depending on the reaction temperature and the solubility of the substrate, and the like. Examples thereof include ether solvents such as diethyl ether, tetrahydrofuran, dioxane and the like, ketone solvents such as acetone, methyl ethyl ketone, methyl isobutyl ketone and the like, carboxylic acid solvents such as acetic acid, propionic acid and the like, ester solvents such as methyl acetate, ethyl acetate, butyl acetate, ethyl propionate and the like, aromatic hydrocarbon solvents such as benzene, toluene, xylene, mesitylene and the like, aromatic halogen solvents such as monochlorobenzene, dichlorobenzene and the like, aliphatic hydrocarbon solvents such as hexane, heptane, octane, cyclohexane and the like, aliphatic halogen solvents such as methylene chloride, chloroform, 1,2-dichloroethane and the like, nitrile solvents such as acetonitrile, propionitrile, benzonitrile and the like, and the like. The solvent may be used alone or in mixture of two or more kinds thereof. From the aspect of reactivity, preferred are aromatic hydrocarbon solvents, aliphatic halogen solvents and nitrile solvents, and more preferred are toluene, methylene chloride, chloroform and acetonitrile, and most preferred are methylene chloride, chloroform and acetonitrile.

While the amount of the solvent to be used is not particularly limited, it is preferably 1 to 50-fold amount (weight standard), more preferably 2 to 10-fold amount (weight standard), relative to compound (1).

The reaction temperature in Step 1 is preferably appropriately set within from the lower limit of about −80° C. to the upper limit of the boiling point of the solvent. From the aspect of the reaction rate and reaction efficiency, it is preferably −30° C. to 120° C., more preferably −30° C. to 80° C., further more preferably −30° C. to 50° C. The reaction time is appropriately set depending on the amounts and kinds of the substrate and solvent, the reaction temperature, and the like. From the aspect of the reaction rate and reaction efficiency, it is preferably 5 min to 24 hr, more preferably 10 min to 6 hr, further more preferably 30 min to 2 hr. The reaction pressure is appropriately set as necessary, and the reaction may be performed under pressure, reduced pressure or atmospheric pressure, preferably atmospheric pressure. While the reaction atmosphere is appropriately selected as necessary, the reaction is preferably performed under an inert gas atmosphere such as nitrogen, argon and the like in order to prevent compound (1) from decomposing.

The crude reaction product obtained by the reaction of compound (1) with compound (2) may be directly used in the next reaction. In order to remove the by-product (e.g., a hydrogen halide, a hydrohalide, etc.) contained in the crude reaction product, the crude product may be washed with water, or the solid salt may be removed by filtration from the crude product. Compound (3) may be isolated and purified from the crude reaction product. As isolation and purification means, methods such as solvent extraction, distillation, sublimation, crystallization, silica gel column chromatography, preparative thin layer chromatography, preparative liquid chromatography, solvent washing and the like, which are publicly or commonly known to those skilled in the art, can be employed.

The solvent used for isolation and purification is preferably selected from solvents in which compound (3) does not decompose, and examples thereof include aliphatic halogen solvents such as dichloromethane, chloroform, 1,2-dichloroethane and the like; aromatic hydrocarbon solvents such as benzene, toluene, xylene, anisole and the like; ether solvents such as diethyl ether, t-butyl methyl ether, diisopropyl ether, 1,2-dimethoxyethane and the like; alcohol solvents such as methanol, ethanol, isopropyl alcohol and the like; aliphatic hydrocarbon solvents such as heptane, hexane, cyclohexane, methylcyclohexane and the like; ester solvents such as ethyl acetate, isopropyl acetate, butyl acetate and the like; nitrile solvents such as acetonitrile, propionitrile and the like, ketone solvents such as methyl isobutyl ketone and the like, water and the like. The solvent may be used alone or in mixture of two or more kinds thereof. Preferred are halogen solvents and ether solvents, and particular preferred are methylene chloride and t-butyl methyl ether.

[Production Step of Compound (3b) from Compound (3a) (Step 1-i)]

As the production method of compound (3), a method of producing compound (3b), which is a compound wherein $Y^1$ in the formula (3) is an oxygen atom, by reacting a compound represented by the following formula (3a), which is a compound wherein $Y^1$ in the formula (3) is $N^+R^7R^8 \cdot A^-$, with water under acidic condition, basic condition or neutral condition, can be employed, in addition to Step 1. Hereinafter, the step of producing compound (3b) from compound (3a) is referred to as Step 1-i. Step 1-i can be employed in view of easy availability and cost of the raw material compound, or in the case of low reaction yield of Step 1 when $Y^1$ is an oxygen atom, and the like.

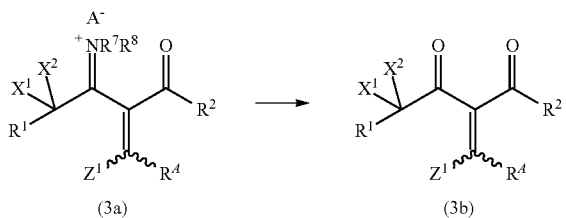

(3a)  (3b)

The definitions and preferable embodiments of $R^1$, $R^2$, $R^7$, $R^8$, $R^4$, $X^1$, $X^2$ and $Z^1$ are as described in Step 1.

When Step 1-i is performed under acidic condition or basic condition, this step can be performed, for example, in the presence of an acid or a base, together with water to be reacted. When the reaction is performed under acidic condition or basic condition, the addition order of compound (3a), water and an acid or a base is not particularly limited as long as compound (3a) does not decompose. For example, compound (3a) may be added to an acidic or basic aqueous solution, or an acid or a base may be added to a mixture of compound (3a) and water. The addition of the acid or base may be batch addition, consecutive addition or continuous addition. Examples of the acid include inorganic acids such as hydrochloric acid, sulfuric acid, nitric acid, phosphoric acid and the like, organic acids such as trifluoroacetic acid, methanesulfonic acid, p-toluenesulfonic acid and the like, and the like. Examples of the base include inorganic bases such as sodium carbonate, sodium hydrogencarbonate, cesium carbonate, sodium hydroxide, potassium hydroxide, cesium hydroxide and the like, organic bases such as triethylamine, pyridine and the like, and the like. The amount of the acid or base to be used is preferably 0.8 to 5.0 mol, more preferably 0.9 to 4.0 mol, further more preferably 1.0 to 2.0 mol, per 1 mol of compound (3a). While the amount of the water to be used is not particularly limited, it is preferably 0.5 to 20-fold amount (weight standard), more preferably 0.8 to 5-fold amount (weight standard), relative to compound (3a)

Step 1-I may be performed under acidic condition, neutral condition or basic condition, preferably under basic condition.

The reaction of compound (3a) with water may be performed in the presence of a solvent. The solvent is preferably selected from solvents inert to the reaction, and is appropriately selected depending on the reaction temperature and the solubility of the substrate, and the like. Examples thereof include ether solvents such as diethyl ether, tetrahydrofuran, dioxane and the like, ketone solvents such as acetone, methyl ethyl ketone, methyl isobutyl ketone and the like, carboxylic acid solvents such as acetic acid, propionic acid and the like, ester solvents such as methyl acetate, ethyl acetate, butyl acetate, ethyl propionate and the like, aromatic hydrocarbon solvents such as benzene, toluene, xylene, mesitylene and the like, aromatic halogen solvents such as monochlorobenzene, dichlorobenzene and the like, aliphatic hydrocarbon solvents such as hexane, heptane, octane, cyclohexane and the like, aliphatic halogen solvents such as methylene chloride, chloroform, 1,2-dichloroethane and the like, nitrile solvents such as acetonitrile, propionitrile, benzonitrile and the like, and the like, and mixed solvents of water and these solvents. The solvent may be used alone or in mixture of two or more kinds thereof. When a mixed solvent of an organic solvent and water is used, the reaction solution may be homogeneous system or two phase system of organic phase-aqueous phase. From the aspect of reactivity, preferred are aromatic hydrocarbon solvents, an aliphatic halogen solvents and nitrile solvents, and more preferred are toluene, methylene chloride and acetonitrile.

While the amount of the solvent to be used is not particularly limited, it is preferably 1 to 50-fold amount (weight standard), more preferably 2 to 10-fold amount (weight standard), relative to compound (3a).

The reaction temperature in Step 1-i is preferably within from the lower limit of about −50° C. to the upper limit of room temperature (25° C.). From the aspect of the reaction rate and reaction efficiency, it is more preferably −20° C. to 0° C. The reaction time is appropriately set depending on the amounts and kinds of the substrate and solvent, the reaction temperature, and the like. From the aspect of the reaction rate and reaction efficiency, it is preferably 5 min to 12 hr, more preferably 30 min to 6 hr. Compound (3b) can be efficiently produced from compound (3a) by Step 1-i.

[Step 2: Production Step of Compound (5) from Compound (3) (Step 2)]

Next, compound (3) is reacted with compound (4a) or compound (4b) to give compound (5). Hereinafter, the step of producing compound (5) from compound (3) is referred to as Step 2.

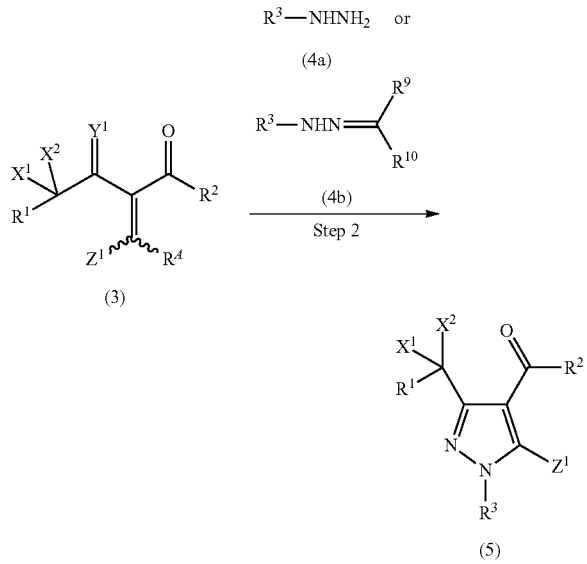

The definitions and preferable embodiments of $R^1$, $R^2$, $R^4$, $X^1$, $X^2$, $Y^1$ and $Z^1$ are as described in Step 1.

In Step 2, compound (3b) is preferably used as compound (3). Compound (3b) has the advantage that production of by-product in the cyclization reaction can be reduced and high yield can be achieved, as compared with compound (3a). Compound (3b) can be synthesized according to Step 1 or Step 1-i.

In compound (4a), $R^3$ is a hydrogen atom, a $C_{1-8}$ alkyl group or a nitrogen-protecting group, and examples thereof include a hydrogen atom, a methyl group, an ethyl group, a n-propyl group, an isopropyl group, a benzoyl group, a t-butoxycarbonyl group and the like. $R^3$ is preferably a hydrogen atom or a $C_{1-8}$ alkyl group, more preferably a hydrogen atom, a methyl group or an ethyl group. Specific examples of compound (4a) include hydrazine (a compound wherein $R^3$ is a hydrogen atom), methylhydrazine (a compound wherein $R^3$ is a methyl group), ethylhydrazine (a compound wherein $R^3$ is an ethyl group) and the like. These can be easily commercially available. Compound (4a) may be a hydrate or an aqueous solution. For example, hydrazine monohydrate or 40% aqueous methylhydrazine solution may be used.

In compound (4b), $R^3$ is a hydrogen atom, a $C_{1-8}$ alkyl group or a nitrogen-protecting group, and examples thereof include a hydrogen atom, a methyl group, an ethyl group, a n-propyl group, an isopropyl group, a benzoyl group, a t-butoxycarbonyl group and the like. $R^3$ is preferably a hydrogen atom or a $C_{1-8}$ alkyl group, more preferably a hydrogen atom, a methyl group or an ethyl group.

$R^9$ and $R^{10}$ are each independently a hydrogen atom, a $C_{1-12}$ alkyl group, a $C_{1-12}$ alkyl group having substituent(s), a $C_{3-8}$ cycloalkyl group, a $C_{3-8}$ cycloalkyl group having substituent(s), an aryl group, an aryl group having substituent(s), a heteroaryl group or a heteroaryl group having substituent(s), or $R^9$ and $R^{10}$ are optionally bonded to each other to form, together with the carbon atom to which they are bonded, a 3- to 8-membered cycloalkane, a 3- to 8-membered cycloalkane having substituent(s), a 3- to 8-membered heterocycle or a 3- to 8-membered heterocycle having substituent(s). $R^9$ and $R^{10}$ are preferably each independently a hydrogen atom, a $C_{1-12}$ alkyl group or an aryl group, or $R^9$ and $R^{10}$ are preferably bonded to each other to form, together with the carbon atom to which they are bonded, a 3- to 8-membered cycloalkane. $R^9$ and $R^{10}$ are more preferably each independently a hydrogen atom, a methyl group, an ethyl group, a t-butyl group or a phenyl group, or $R^9$ and $R^{10}$ are more preferably bonded to each other to form, together with the carbon atom to which they are bonded, cyclopentane or cyclohexane. $R^9$ and $R^{10}$ are further more preferably each independently a hydrogen atom, a methyl group or an ethyl group, or $R^9$ and $R^{10}$ are further more preferably bonded to each other to form, together with the carbon atom to which they are bonded, cyclopentane or cyclohexane.

Specific examples of compound (4b) include a compound wherein $R^3$ is a methyl group, and $R^9$ and $R^{10}$ are both methyl groups, a compound wherein $R^3$ is a methyl group, and $R^9$ and $R^{10}$ are bonded to each other to form cyclohexane, together with the carbon atom to which they are bonded, a compound wherein $R^3$ is a methyl group, $R^9$ is a methyl group, and $R^{10}$ is an ethyl group, a compound wherein $R^3$ is a methyl group, $R^9$ is a hydrogen atom, and $R^{10}$ is a phenyl group, a compound wherein $R^3$ is a methyl group, $R^9$ is a methyl group, and $R^{10}$ is a t-butyl group, and the like.

Compound (4b) can be synthesized according to a known method, for example, the method described in JP 2011-513446.

In Step 2, the addition order of compound (3) and compound (4a) or compound (4b) is not particularly limited. Compound (4a) and compound (4b) are used alone or in combination. The ratio in combination use is not particularly limited. The amount of compound (4a) or compound (4b) to be used is not particularly limited. From the aspect of economy, it is preferably 0.8 to 3.0 mol, more preferably 0.9 to 2.0 mol, further more preferably 1.0 to 1.8 mol, particularly preferably 1.0 to 1.5 mol, per 1 mol of compound (3). Total amount of compound (4a) and compound (4b) in combination use is preferably 0.8 to 3.0 mol, more preferably 0.9 to 2.0 mol, further more preferably 1.0 to 1.8 mol, particularly preferably 1.0 to 1.5 mol, per 1 mol of compound (3).

The reaction of compound (3) with compound (4a) or compound (4b) may be performed in the presence of a solvent. The solvent is preferably selected from solvents inert to the reaction, and is appropriately selected depending on the reaction temperature and the solubility of the substrate, and the like. Examples thereof include ether solvents such as diethyl ether, tetrahydrofuran, dioxane and the like, carboxylic acid solvents such as acetic acid, propionic acid and the like, ester solvents such as methyl acetate, ethyl acetate, butyl acetate, ethyl propionate and the like, aromatic hydrocarbon solvents such as benzene, toluene, xylene, mesitylene and the like, aromatic halogen solvents such as monochlorobenzene, dichlorobenzene and the like, aliphatic hydrocarbon solvents such as hexane, heptane, octane, cyclohexane and the like, aliphatic halogen solvents such as methylene chloride, chloroform, 1,2-dichloroethane and the like, nitrile solvents such as acetonitrile, propionitrile, benzonitrile and the like, and the like, and mixed solvents of water and these solvents. The solvent may be used alone or in mixture of two or more kinds thereof. When a mixed solvent of an organic solvent and water is used, the reaction solution may be homogeneous system or two phase system of organic phase-aqueous phase. From the aspect of reactivity, preferred are aliphatic halogen solvents and nitrile solvents, and more preferred are methylene chloride, chloroform and acetonitrile.

While the amount of the solvent to be used is not particularly limited, it is preferably 1 to 50-fold amount (weight standard), more preferably 2 to 10-fold amount (weight standard), relative to compound (3).

The reaction temperature in Step 2 is preferably appropriately set within from the lower limit of the freezing point of the solvent to the upper limit of the boiling point of the solvent. From the aspect of the reaction rate and reaction efficiency, it is preferably −50° C. to 50° C., more preferably −40° C. to room temperature (about 25° C.), particularly preferably −40° C. to 0° C. The reaction time is appropriately set depending on the amounts and kinds of the substrate and solvent, the reaction temperature, and the like. From the aspect of the reaction rate and reaction efficiency, it is preferably 5 min to 24 hr, more preferably 10 min to 8 hr, further more preferably 30 min to 4 hr. The reaction pressure is appropriately set as necessary, and the reaction may be performed under pressure, reduced pressure or atmospheric pressure, preferably atmospheric pressure. While the reaction atmosphere is appropriately selected as necessary, the reaction is preferably performed in an air or under an inert gas atmosphere such as nitrogen, argon and the like.

In the reaction of Step 2, a compound represented by the following formula (5-imp1), (5-imp2), (5-imp3), (5-imp4) or (5-imp5) was expected to be theoretically produced as a cyclization by-product, in addition to compound (5).

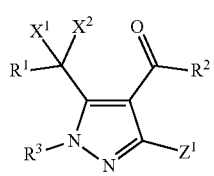
5-imp1

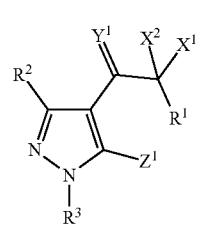
5-imp2

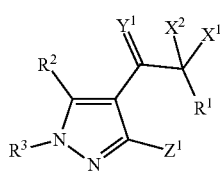
5-imp3

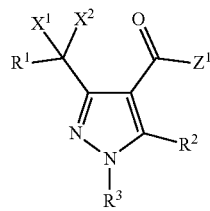
5-imp4

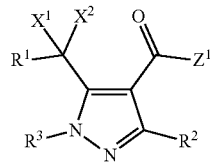
5-imp5

$R^1$, $R^2$, $R^3$, $X^1$, $X^2$, $Z^1$ and $Y^1$ are as defined above.

However, the reaction of Step 2 in the production method of the present invention can proceed with unexpectedly high selectivity. Therefore, in Step 2, the objective compound (5) can be obtained in high-yield. That is to say, the amount of the cyclization by-product relative to the total amount of compound (5) and the cyclization by-product is less than 5 mol %, particularly less than 3 mol %, and therefore, high-yield can be achieved.

The reaction of compound (3) with compound (4a) or compound (4b) may be performed in the presence of a base.

Examples of the base include organic bases and inorganic bases. Examples of the organic base include chain secondary or tertiary amines such as dimethylamine, trimethylamine, triethylamine, diisopropylethylamine, tert-butyldimethylamine, ethyldicyclohexylamine and the like; cyclic tertiary amines such as N-methylpyrrolidine, N-methylpiperidine, N-methylmorpholine, N,N'-dimethylpiperazine, pyridine, collidine, lutidine, 4-dimethylaminopyridine and the like; bicyclic amines such as diazabicycloundecene (DBU), diazabicyclononene (DBN) and the like; and the like.

Examples of the inorganic base include ammonia, alkali metal and alkaline-earth metal hydroxides such as sodium hydroxide, potassium hydroxide, calcium hydroxide and the like; alkali metal and alkaline-earth metal oxides such as lithium oxide, sodium oxide, calcium oxide, magnesium oxide and the like; alkali metal and alkaline-earth metal carbonates such as lithium carbonate, calcium carbonate and the like; alkali metal bicarbonates such as sodium bicarbonate, potassium bicarbonate and the like; alkali metal and alkaline-earth metal hydrides such as lithium hydride, sodium hydride, potassium hydride, calcium hydride and the like; alkali metal amides such as lithium amide, sodium amide, potassium amide and the like; and the like.

As the base, from the aspect of selectivity improvement, preferred are organic bases, more preferred are ammonia and chain secondary or tertiary amines, particularly preferred are chain secondary or tertiary amines, further preferred are chain secondary amines, and most preferred is dimethylamine.

While the amount of the base to be used is not particularly limited, it is preferably 0.001 to 10 mol, more preferably 0.1 to 5 mol, further more preferably 0.2 to 3 mol, per 1 mol of compound (3).

When the reaction of compound (3) with compound (4a) or compound (4b) is performed in the presence of a base, production of cyclization by-product, i.e., compound (5-imp1), compound (5-imp2), compound (5-imp3), compound (5-imp4), compound (5-imp5) and the like can be reduced, and therefore, compound (5) can be obtained with high selectivity in high-yield.

The crude reaction product obtained by the reaction of compound (3) with compound (4a) or compound (4b) may be directly used in the next reaction. Alternatively, compound (5) may be isolated and purified from the crude reaction product. As isolation and purification means, methods such as solvent extraction, distillation, sublimation, crystallization, silica gel column chromatography, preparative thin layer chromatography, preparative liquid chromatography, washing with solvent and the like, which are publicly or commonly known to those skilled in the art, can be employed.

The solvent used for isolation and purification is preferably selected from solvents which do not affect the stability and recovery rate of the reaction product as far as possible, and examples thereof include aromatic halogen solvents such as monochlorobenzene, dichlorobenzene and the like; aliphatic halogen solvents such as dichloromethane, chloroform, 1,2-dichloroethane and the like; aromatic hydrocarbon solvents such as benzene, toluene, xylene, anisole and the like; ether solvents such as diethyl ether, t-butyl methyl ether, diisopropyl ether, 1,2-dimethoxyethane and the like; alcohol solvents such as methanol, ethanol, isopropyl alcohol and the like; aliphatic hydrocarbon solvents such as heptane, hexane, cyclohexane, methylcyclohexane and the like; ester solvents such as ethyl acetate, isopropyl acetate, butyl acetate and the like; nitrile solvents such as acetonitrile, propionitrile and the like; ketone solvents such as methyl isobutyl ketone and the like; water and the like. The solvent may be used alone or in mixture of two or more kinds thereof. Preferred are ester solvents, aliphatic halogen solvents, aliphatic hydrocarbon solvents, water and mixed solvents thereof, and more preferred are a combination of a solvent selected from chloroform, ethyl acetate, toluene and water and a solvent selected from heptane, methylcyclohexane and ethylcyclohexane, and further more preferred are a mixed solvent of chloroform and methylcyclohexane, a mixed solvent of heptane and ethyl acetate, a combination of water and an aliphatic hydrocarbon solvent, and the like, and most preferred is a combination of chloroform and methylcyclohexane.

[Production Step of Compound (6) from Compound (5) (Step 3)]

Compound (6) can be produced by reacting compound (5) with an oxidant. Hereinafter, the step of producing compound (6) from compound (5) is referred to as Step 3. The reaction concept of Step 3 can be shown by the following formula. When the reaction is performed under basic condition, compound (5) is converted to a compound represented by the following formula (6a), and then compound (6a) is reacted with an acid to give compound (6).

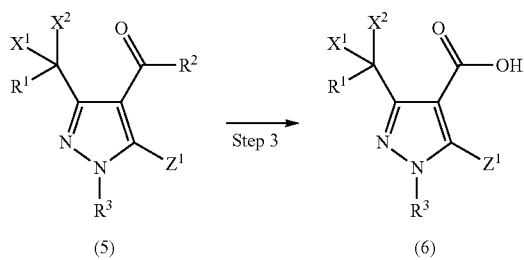

-continued
Step 3

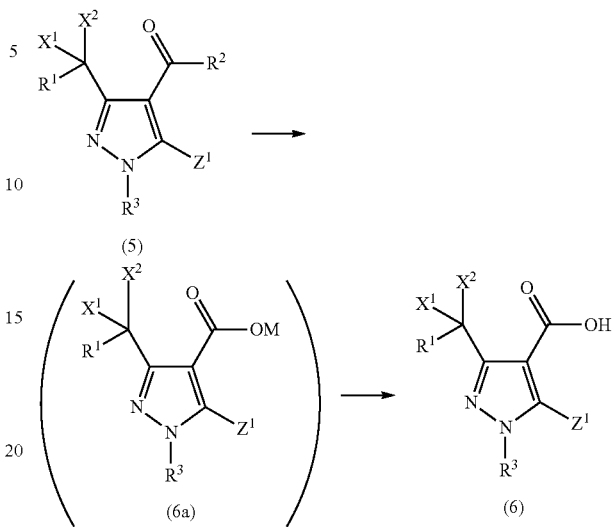

The definitions and preferable embodiments of $R^1$, $R^2$, $X^1$, $X^2$ and $Z^1$ are as described in Step 1, the definitions and preferable embodiments of $R^3$ are as described in Step 2, and M is a counter cation of a carboxylic acid, and examples thereof include $Na^+$, $K^+$, $\frac{1}{2}Ca^{2+}$, $NH_4^+$ and the like.

The oxidant is not particularly limited, and preferable examples thereof include halogens (chlorine, bromine, iodine), halogen oxoacids and salts thereof (hypochlorous acid and a salt thereof, hypobromous acid and a salt thereof, chlorous acid and a salt thereof, chloric acid and a salt thereof, iodic acid and a salt thereof, periodic acid and a salt thereof, etc.), peroxides (hydrogen peroxide, etc.), oxygen molecule, ozone and the like. Examples of the counter cation of the oxoacid salt include $Na^+$, $K^+$, $\frac{1}{2}Ca^{2+}$, $NH_4^+$ and the like.

The oxidant is preferably an oxidant containing chlorine, more preferably hypochlorous acid or a salt thereof, particularly preferably a hypochlorite.

The oxidation reaction may be performed under acidic condition, neutral condition or basic condition. When basic condition is employed, for example, when a basic oxidant is used as an oxidant, or when the oxidation reaction is performed in the presence of a base, the carboxylate compound (6a) is produced from compound (5), and then is converted to compound (6) by the reaction with an acid.

Examples of the base include inorganic base and organic base. Examples of the inorganic base include alkali metal and alkaline-earth metal hydroxides such as sodium hydroxide, potassium hydroxide, calcium hydroxide and the like; alkali metal and alkaline-earth metal oxides such as lithium oxide, sodium oxide, calcium oxide, magnesium oxide and the like; alkali metal and alkaline-earth metal carbonates such as lithium carbonate, calcium carbonate and the like; alkali metal bicarbonates such as sodium bicarbonate, potassium bicarbonate and the like; alkali metal and alkaline-earth metal hydrides such as lithium hydride, sodium hydride, potassium hydride, calcium hydride and the like; alkali metal amides such as lithium amide, sodium amide, potassium amide and the like; and the like. Examples of the organic base include amines such as triethylamine, dimethylamine and the like, and ammonia. From the aspect of cost, preferred are alkali metal and alkaline-earth metal hydroxides, alkali metal and alkaline-earth metal oxides, alkali metal and alkaline-earth metal carbonates and alkali metal bicarbonates, and more preferred are alkali metal and alkaline-earth metal hydroxides, and most preferred are sodium hydroxide, potassium hydroxide and calcium hydroxide.

When compound (5) causes side reaction under acidic condition, for example when chlorination or decarboxylation proceeds at undesirable moiety by the oxidation using chlorine under acidic condition, the reaction is preferably performed under basic condition.

In the method of reacting under basic condition, a hypochlorite, which is used as an oxidant, is generally commercially available as a basic aqueous solution, and it generates a basic compound with progression of the reaction, and therefore, the reaction system becomes basic. In addition, a hypochlorite can be prepared by reacting an aqueous sodium hydroxide solution or an aqueous potassium hydroxide solution with chlorine.

The addition order of compound (5) and the oxidant is not particularly limited. When the reaction intermediate decomposes easily under oxidant-poor condition, compound (5) is preferably added to an oxidant. While the amount of the oxidant to be used is not particularly limited, it is preferably 1 to 10 mol, per 1 mol of compound (5).

The reaction of compound (5) with an oxidant may be performed in the presence of a solvent. The solvent is preferably selected from solvents inert to the reaction, and is appropriately selected depending on the reaction temperature and the solubility of the substrate, and the like. Examples thereof include ether solvents such as diethyl ether, tetrahydrofuran, dioxane and the like; ketone solvents such as acetone, methyl ethyl ketone, methyl isobutyl ketone and the like; carboxylic acid solvents such as acetic acid, propionic acid and the like; ester solvents such as methyl acetate, ethyl acetate, butyl acetate, ethyl propionate and the like; aromatic hydrocarbon solvents such as benzene, toluene, xylene, mesitylene and the like; aromatic halogen solvents such as monochlorobenzene, dichlorobenzene and the like; aliphatic hydrocarbon solvents such as hexane, heptane, octane, cyclohexane and the like; aliphatic halogen solvents such as methylene chloride, chloroform, carbon tetrachloride, 1,2-dichloroethane and the like; nitrile solvents such as acetonitrile, propionitrile, benzonitrile and the like; and water. The solvent may be used alone or in mixture of two or more kinds thereof. Preferred are ether solvents, aliphatic halogen solvents and water, and particularly preferred are tetrahydrofuran, dioxane, chloroform, carbon tetrachloride and water. From the aspect of cost and easy isolation and purification after the reaction, most preferred are chloroform and water.

While the amount of the solvent to be used is not particularly limited, it is preferably 1 to 50-fold amount (weight standard), more preferably 2 to 15-fold amount (weight standard), relative to compound (5).

The reaction temperature in Step 3 is preferably appropriately set within from the lower limit of −30° C., preferably 00° C., to the upper limit of the boiling point of the solvent. From the aspect of the reaction rate and reaction efficiency, it is preferably −20 to 120° C., more preferably 0 to 70° C. The reaction time is appropriately set depending on the amounts and kinds of the substrate, oxidant and solvent, the reaction temperature, and the like. From the aspect of the reaction rate and reaction efficiency, it is preferably 5 min to 24 hr, more preferably 10 min to 8 hr, further more preferably 30 min to 4 hr. The reaction pressure is appropriately set as necessary, and the reaction may be performed under pressure, reduced pressure or atmospheric pressure, preferably atmospheric pressure. While the reaction atmosphere is appropriately selected as necessary, the reaction is preferably performed in an air or under an inert gas atmosphere such as nitrogen, argon and the like.

For the promotion of the reaction, a phase-transfer catalyst may be used. As a phase-transfer catalyst, known compounds such as quaternary ammonium salts may be used, or compound (6) or intermediate compound (6a) produced in Step 3 may be used. The addition of the phase-transfer catalyst is particularly effective when compound (5) is hardly soluble in water, or when the reaction is performed in two phase system using water and an organic solvent incompatible with water as solvents. The compound hardly soluble in water means a compound having solubility of about 2% or less in water. While the amount of the phase-transfer catalyst to be used is not particularly limited, it is generally 0.001 to 1 mol, preferably 0.01 to 0.1 mol, per 1 mol of compound (5).

When the reaction of compound (5) with an oxidant is performed under basic condition, the next reaction of compound (6a) with an acid may be performed by adding an acid to the post-treated reaction mixture after the completion of the oxidation reaction, or by adding an acid to the reaction system containing compound (6a) after the completion of the oxidation reaction.

The acid is preferably one having sufficient acidity to produce a carboxylic acid, for example, inorganic acids such as hydrochloric acid, sulfuric acid, nitric acid, phosphoric acid and the like, or organic acids such as trifluoroacetic acid, methanesulfonic acid, p-toluenesulfonic acid and the like.

The amount of the acid to be used is a sufficient amount to convert compound (6a) to compound (6), preferably a sufficient amount to acidify the system after the addition of the acid to pH 5 or low, preferably pH 3 or low.

Compound (6) obtained as a free carboxylic acid by the above-mentioned method has well high purity without purification, and higher purity can be achieved by solvent washing using water and the like.

Compound (6) can also be isolated and purified from the crude reaction product obtained by the reaction of compound (5) with an oxidant. As isolation and purification means, methods such as solvent extraction, distillation, sublimation, crystallization, silica gel column chromatography, preparative thin layer chromatography, preparative liquid chromatography, solvent washing and the like, which are publicly or commonly known to those skilled in the art, can be employed.

The solvent used for isolation and purification is preferably selected from the solvents in which compound (6) does not decompose, and examples thereof include aliphatic halogen solvents such as dichloromethane, chloroform, 1,2-dichloroethane and the like; aromatic hydrocarbon solvents such as benzene, toluene, xylene, anisole and the like; ether solvents such as diethyl ether, t-butyl methyl ether, diisopropyl ether, 1,2-dimethoxyethane and the like; alcohol solvents such as methanol, ethanol, isopropyl alcohol and the like; aliphatic hydrocarbon solvents such as heptane, hexane, cyclohexane, methylcyclohexane and the like; ester solvents such as ethyl acetate, isopropyl acetate, butyl acetate and the like; nitrile solvents such as acetonitrile, propionitrile and the like; ketone solvents such as methyl isobutyl ketone and the like, water and the like. The solvent may be used alone or in mixture of two or more kinds thereof. The solvent used for solvent washing is preferably water.

[Intermediate Compound]

Among compound (5) produced by the reaction of compound (3) with compound (4a) or (4b), a compound represented by the following formula (5a) is a novel and useful compound. The present invention provides a novel compound represented by the following formula (5a).

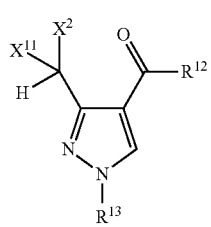

(5a)

$R^{12}$ is a $C_{1-8}$ alkyl group, preferably a methyl group, an ethyl group, a propyl group or an isopropyl group, more preferably a methyl group or an ethyl group, further more preferably a methyl group.

$R^{13}$ is a hydrogen atom, a $C_{1-8}$ alkyl group or a nitrogen-protecting group, preferably a hydrogen atom or a $C_{1-8}$ alkyl group, more preferably a hydrogen atom, a methyl group or an ethyl group, further more preferably a methyl group.

$X^{11}$ and $X^{12}$ are each independently a fluorine atom or a chlorine atom, preferably a fluorine atom.

Provided that compound (5a) wherein $R^{12}$ is a methyl group, $R^{13}$ is a nitrogen-protecting group, and $X^{11}$ and $X^{12}$ are both fluorine atoms is excluded.

Specific examples of compound (5a) include the following compounds.
1-(3-difluoromethyl-1-methyl-1H-pyrazol-4-yl)-1-propanone,
1-(3-difluoromethyl-1-methyl-1H-pyrazol-4-yl)-1-butanone,
1-(3-difluoromethyl-1-methyl-1H-pyrazol-4-yl)-2-methyl-1-propanone,
1-(3-difluoromethyl-1H-pyrazol-4-yl)ethanone,
1-(3-difluoromethyl-1H-pyrazol-4-yl)-1-propanone,
1-(3-difluoromethyl-1H-pyrazol-4-yl)-1-butanone, and
1-(3-difluoromethyl-1H-pyrazol-4-yl)-2-methyl-1-propanone.

Among compound (3) produced by the reaction of compound (1) with compound (2), a compound represented by the following formula (3c) is a novel and useful compound. The present invention provides a novel compound represented by the following formula (3c).

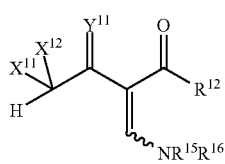

(3c)

In compound (3c), $R^{12}$ is a $C_{1-8}$ alkyl group, preferably a methyl group, an ethyl group, a propyl group or an isopropyl group, more preferably a methyl group or an ethyl group, further more preferably a methyl group.

$R^{15}$ and $R^{16}$ are each independently a hydrogen atom or a $C_{1-8}$ alkyl group, or $R^{15}$ and $R^{16}$ are optionally bonded to each other to form, together with the nitrogen atom to which they are bonded, a 5- to 6-membered heterocycle. $R^{15}$ and $R^{16}$ are preferably each independently a hydrogen atom, a methyl group or an ethyl group, or $R^{15}$ and $R^{16}$ are preferably bonded to each other to form, together with the nitrogen atom to which they are bonded, pyrrolidine, piperidine or morpholine.

$X^{11}$ and $X^{12}$ are each independently a fluorine atom or a chlorine atom, preferably a fluorine atom.

$Y^{11}$ is an oxygen atom or $N^+R^7R^8 \cdot A^-$, preferably an oxygen atom. $R^{17}$ and $R^{18}$ are each independently a $C_{1-8}$ alkyl group, or $R^{17}$ and $R^{18}$ are optionally bonded to each other to form, together with the nitrogen atom to which they are bonded, a 5- to 6-membered heterocycle. $R^{17}$ and $R^{18}$ are preferably each independently a methyl group or an ethyl group, or $R^{17}$ and $R^{18}$ are preferably bonded to each other to form, together with the nitrogen atom to which they are bonded, pyrrolidine, piperidine or morpholine.

$A^-$ is a counter anion, preferably a halide ion such as a fluoride ion, a chloride ion or the like, or a tetrafluoroborate ion ($BF_4^-$).

The wavy line in formula (3c) means that the configuration of $NR^{15}R^{16}$ relating to the double bond is E or Z.

Among them, a compound wherein $R^{12}$ is a $C_{1-8}$ alkyl group, $R^{15}$ and $R^{16}$ are each independently a $C_{1-8}$ alkyl group, $X^{11}$ and $X^{12}$ are both fluorine atoms, and $Y^{11}$ is an oxygen atom is particularly preferable.

Specific examples of compound (3c) include the following compounds.

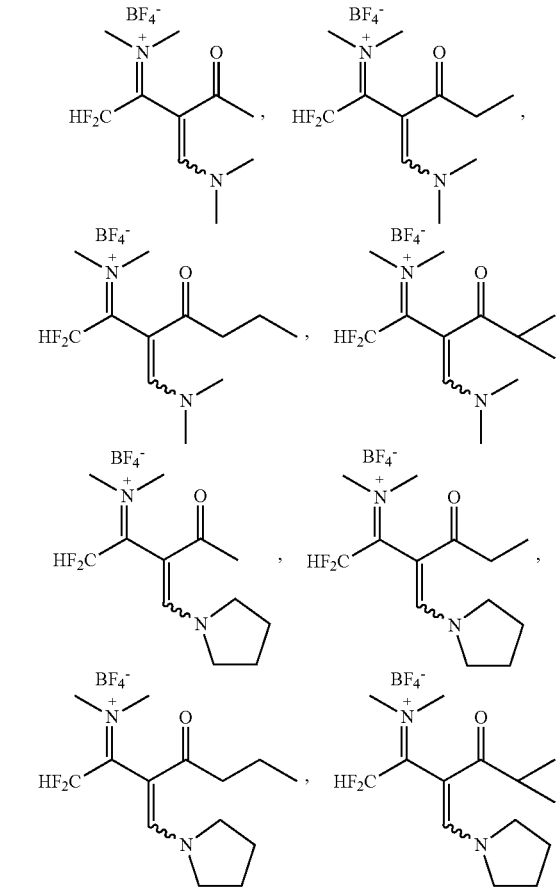

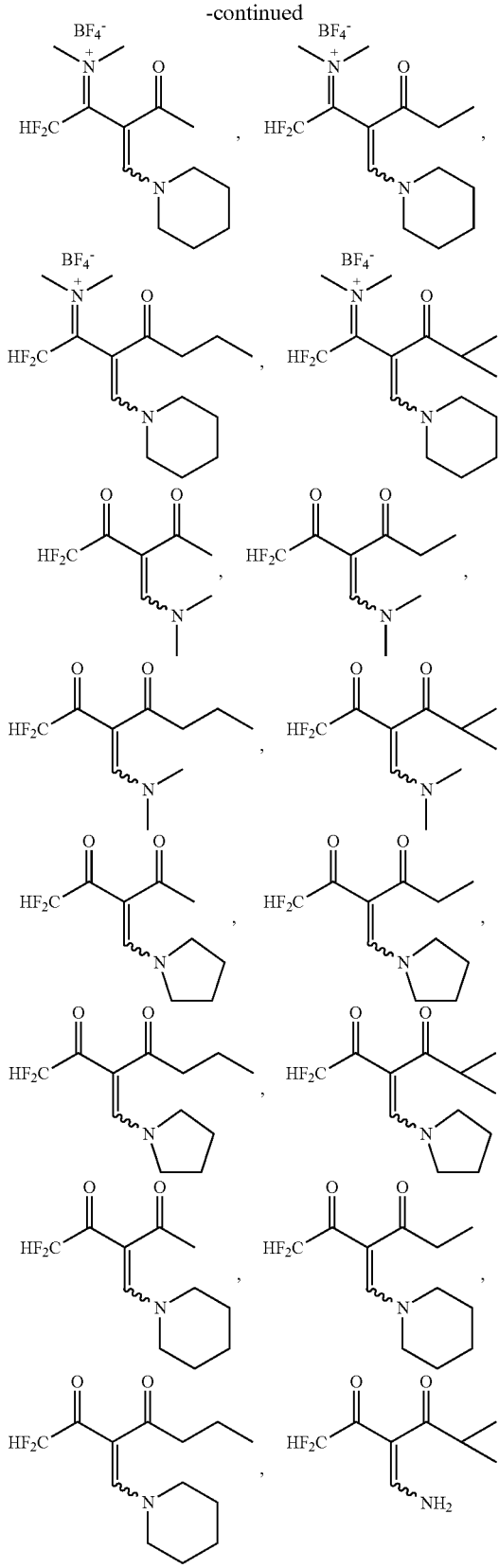

Among compound (3) produced by the reaction of compound (1) with compound (2), a compound represented by the following formula (3d) is a novel and useful compound.

The present invention provides a novel compound represented by the following formula (3d).

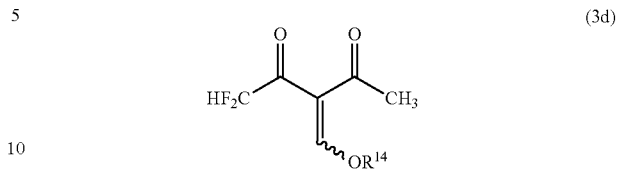

In compound (3d), $R^{14}$ is a $C_{1-2}$ alkyl group, i.e., an ethyl group or a methyl group.

The wavy line in formula (3d) means that the configuration of $OR^{14}$ relating to the double bond is E or Z.

Specific examples of compound (3d) include the following compounds.

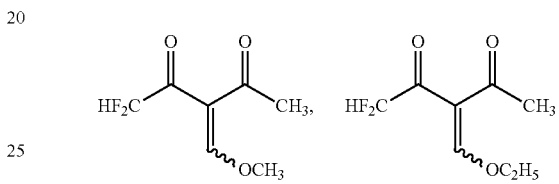

Compound (3c), compound (3d) and compound (5a) are intermediate compounds useful for the production method of the present invention. 4-Keto pyrazole derivatives and pyrazole-4-carboxylic acid derivatives obtained from these intermediates are also useful as an intermediate for medicines or agrichemicals. In addition, since compound (3c), compound (3d) and compound (5a) are easily produced from inexpensive raw materials, and they have easy handling, the production methods using these intermediates are industrially excellent.

In the present invention, the following compound (2n) may be used instead of compound (2). When compound (2n) is used, the compound corresponding to compound (3) is the following compound (3n), and the compound corresponding to compound (5) is the following compound (5n). Compound (5) may be produced by subjecting compound (5n) to hydrolysis.

In the formulas, $R''$ is a carbonyl-protecting group capable of being eliminated by hydrolysis, for example, acetal protecting groups such as 1,3-dioxane and the like; monothioacetal protecting group such as 1,3-oxathiolane and the like; dithioacetal protecting groups such as 1,3-dithiane and the like; or hydrazone protecting groups such as methylhydrazone and the like. The other symbols are as defined above.

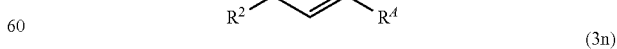

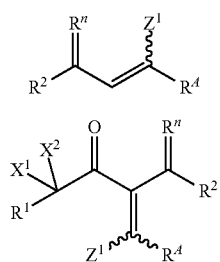

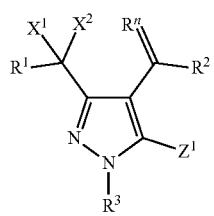

Specific examples of compound (2n) include the following compounds.

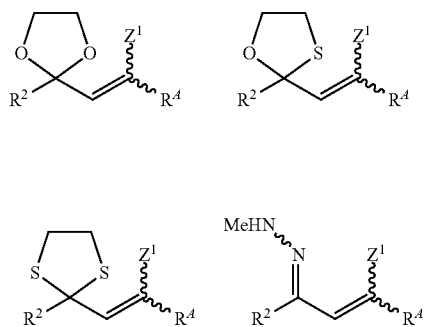

Specific examples of compound (3n) include the following compounds.

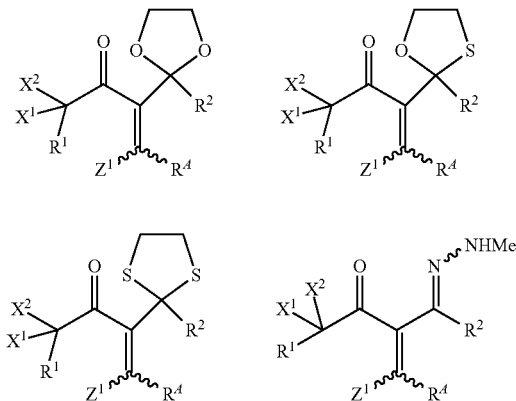

Specific examples of compound (5n) include the following compounds.

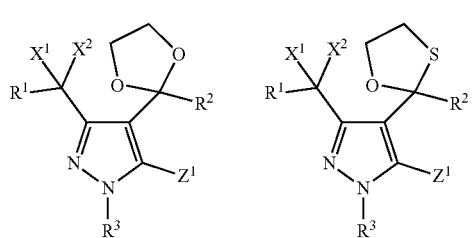

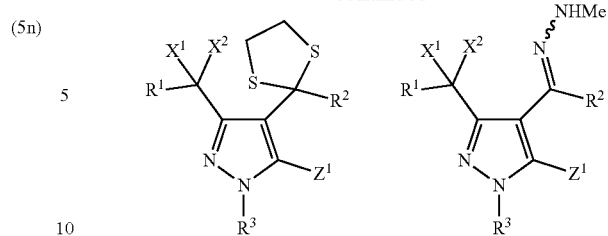

EXAMPLES

The present invention is explained in detail in the following by referring to Examples, which are not to be construed as limitative. The term "compound n" means a compound represented by the formula (n).

JNM-ECP400 (400 MHz) manufactured by JEOL Ltd. is used for NMR analysis in Examples and Comparative Examples. For $^1$H NMR, tetramethylsilane is used as a standard substance (0 PPM), and for $^{19}$F NMR, $C_6F_6$ is used as a standard substance (−162 PPM). 1260LC or 1200LC manufactured by Agilent or LC-20 manufactured by Shimadzu Corporation is used for HPLC. In Example, the unit of yield (%) is mol %, and the concentration unit of the reaction reagent is weight concentration (wt %).

Example 1

Synthesis of Compound (3b-1) by Reaction of Difluoroacetyl Fluoride (1a-1) and Compound (2b-1)

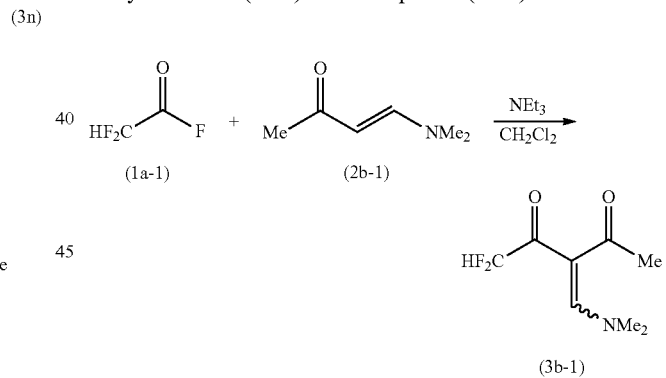

A solution of compound (2b-1) (17.6 g, 140.0 mmol) and triethylamine (57.5 g, 567.9 mmol) in methylene chloride (200 ml) was ice-cooled under nitrogen atmosphere, and difluoroacetyl fluoride (1a-1) (13.7 g, 140.0 mmol) was added thereto. The mixture was stirred at room temperature (25° C.) for 1 hr, and ice-cooled. The reaction was quenched with tap water (100 ml), and the mixture was separated. The aqueous phase was extracted once with methylene chloride (100 ml), and the organic phases were combined. It was confirmed that compound (3b-1) was produced in the yield of 96% based on compound (2b-1) by quantitative analysis of the organic phase using GC.

$^1$H NMR (CD$_3$OD)

δ=2.28 (s, 3H), 2.80 (s, 3H), 3.30 (S, 3H), 6.49 (t, 1H), 8.04 (s, 1H). $^{19}$F NMR (CD$_3$OD) δ=−123.6 (d, 2F).

Example 2

Synthesis of Compound (5-1) by Reaction of Compound (3b-1) with Methylhydrazine

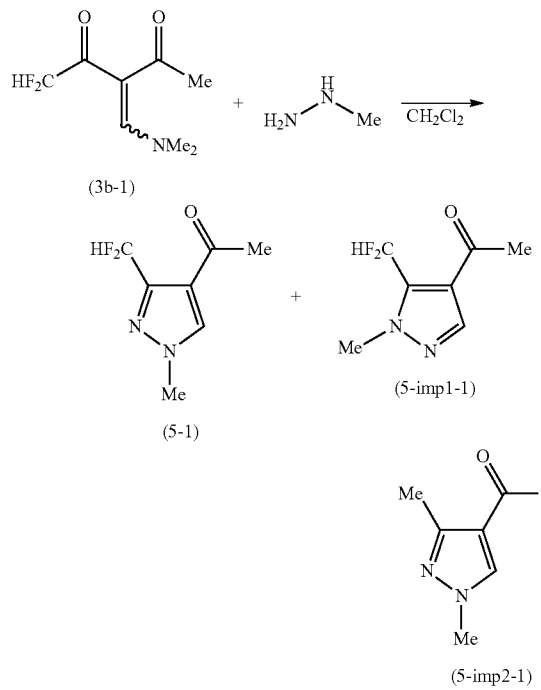

To 40% aqueous methylhydrazine solution (4:0 g, 34.5 mmol) was added methylene chloride (15 ml) under nitrogen atmosphere, and the mixture was cooled to −20° C. A solution of compound (3b-1) (6.0 g, 31.4 mmol, obtained by the above-mentioned method) in methylene chloride (15 ml) was slowly added dropwise thereto, the mixture was stirred at −20° C. for 2 hr, and the reaction was quenched with water (30 ml). The reaction mixture was separated, and the aqueous phase was extracted twice with methylene chloride (15 ml). The organic phases were combined, and washed with saturated brine (15 ml). The organic phase was dried over sodium sulfate, and the solvent was evaporated under reduced pressure. It was confirmed that compound (5-1) was produced in the yield of 86%, and that compound (5-imp1-1) was produced in the yield of 2%, and compound (5-imp2-1) was produced in a trace amount (less than 1%), which are by-products of the cyclization, by analysis of the obtained crude product using NMR and HPLC.

Compound (5-1)
$^1$H NMR (deuterated acetone)
δ=2.41 (s, 3H), 3.99 (s, 3H), 7.17 (t, 1H), 8.41 (s, 1H).
$^{19}$F NMR (deuterated acetone) δ=−113.8 (d, 2F).
Compound (5a-1)
$^{19}$F NMR (deuterated acetone) δ=−114.4 (d, 2F).

Example 2-2

Synthesis of Compound (5-1) by Continuous Reaction of Difluoroacetyl Fluoride (1a-1) in a Single Reactor (One-Pot Method)

A solution of compound (2b-1) (50.0 g, purity 97.6 wt %, 431.3 mmol) and triethylamine (109.1 g, 1078.1 mmol) in methylene chloride (250 mL) was ice-cooled under nitrogen atmosphere, and difluoroacetyl fluoride (1a-1) (67.64 g, 690.1 mmol, synthesized from ethyl-1,1,2,2-tetrafluoroethyl ether) was added thereto without isolation. The mixture was stirred at 25° C. for 20 min, and a part of the obtained crude solution (total 534.8 g) was used directly in the next step. It was confirmed that compound (3b-1) was produced in the yield of 96.3% based on compound (2b-1) by quantitative analysis of the crude solution using NMR.

To 40% aqueous methylhydrazine solution (2.01 g, 17.3 mmol) was added methylene chloride (7.5 mL) under nitrogen atmosphere, and the mixture was cooled to −20° C. A part of the crude solution (27.6 g, containing 15.7 mmol of compound (3b-1)) obtained by the above-mentioned method was slowly added dropwise thereto, and the mixture was stirred at −20° C. for 2 hr. 40% Aqueous methylhydrazine solution (1.28 g, 11.0 mmol) was added thereto, and the mixture was added at −20° C. for 3 hr. The reaction was quenched with water (8 mL), the reaction mixture was separated, and the aqueous phase was extracted twice with methylene chloride (5 mL). The organic phases were combined, and the solvent was evaporated under reduced pressure to give the objective compound (5-1).

Example 3

Synthesis of Compound (6-1) by Oxidation of Compound (5-1) Using NaOCl

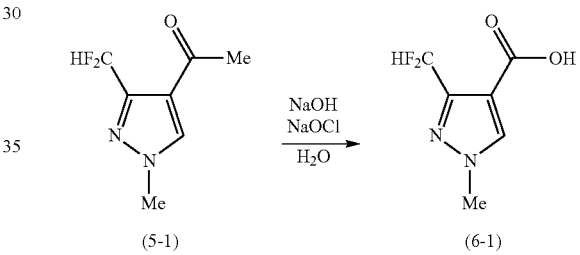

To a mixture of sodium hydroxide (0.72 g, 18.0 mmol) and 8% aqueous sodium hypochlorite solution (16.2 g, 17.5 mmol) was added compound (5-1) (1.01 g, 5.7 mmol, obtained by the method of [Example 2]) at room temperature (25° C.) under air atmosphere, and the mixture was stirred at 70° C. for 2 hr. The reaction mixture was ice-cooled, and the reaction was quenched with saturated aqueous sodium sulfite solution (5 ml). To the aqueous phase was added conc. hydrochloric acid (33 g), and the mixture was extracted twice with isopropyl acetate (30 ml). The solvent was evaporated under reduced pressure. It was confirmed that the yield of compound (6-1) was 98% by analysis of the obtained crude product using HPLC.

$^1$H NMR (CD$_3$OD) δ=3.95 (s, 3H), 7.13 (t, 1H), 8.15 (s, 1H).
$^{19}$F NMR (CD$_3$OD) δ=−114.2 (d, 2F).

Example 3-2

Synthesis of Compound (6-1) by Oxidation of Compound (5-1)

To 14% aqueous sodium hypochlorite solution (18.2 g, 34.4 mmol, pH11) was added compound (5-1) (2.01 g, 11.5 mmol, obtained by the method of [Example 2]) at 20° C. under air atmosphere. The mixture was stirred at 20° C. for 2 hr, and ice-cooled, chloroform (10 mL) was added thereto, and the mixture was separated. The obtained aqueous phase was ice-cooled, and saturated aqueous sodium sulfite solution (5 ml) was added thereto, and the mixture was stirred. The mixture was acidified (pH=1) with 35% hydrochloric acid (2.5 g), and thereby, compound (6-1) was precipitated. The mixture was stirred at 0° C. for 1 hr, and filtered under reduced pressure, and the obtained crude product was washed with water. The solvent was evaporated under reduced pressure to give compound (6-1). The yield was 97%, and the HPLC purity was 99.9%.

$^1$H NMR (CD$_3$OD) δ=3.95 (s, 3H), 7.13 (t, 1H), 8.15 (s, 1H).

$^{19}$F NMR (CD$_3$OD) δ=−114.2 (d, 2F).

Example 4

Synthesis of Compound (6-1) by Oxidation of Compound (5-1) Using NaOCl Prepared from Chlorine Gas and Sodium Hydroxide in System

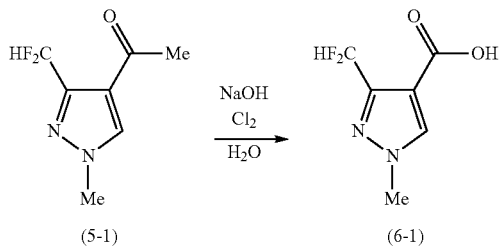

Compound (5-1) (1.85 g, 10.6 mmol, obtained by the method of [Example 2]) was suspended in 20 wt % aqueous sodium hydroxide solution (92 g, 459 mmol) under air atmosphere, and chlorine gas (3.1 g, 43.1 mmol) was added thereto at room temperature (25° C.). The reaction mixture was ice-cooled, and the reaction was quenched with saturated aqueous sodium sulfite solution. To the aqueous phase was added conc. hydrochloric acid, and the mixture was extracted twice with methylene chloride (40 ml). The solvent was evaporated under reduced pressure. It was confirmed that the yield of compound (6-1) was 89% by analysis of the obtained crude product using HPLC.

$^1$H NMR (CD$_3$OD) δ=3.95 (s, 3H), 7.13 (t, 1H), 8.15 (s, 1H).

$^{19}$F NMR (CD$_3$OD) δ=−114.2 (d, 2F).

Example 5

Synthesis of Vinamidinium Salt (3a-1) by Reaction of 1,1,2,2-Tetrafluoro-N,N-Dimethylethanamine (TFEDMA) with BF$_3$, and then with Compound (2b-1)

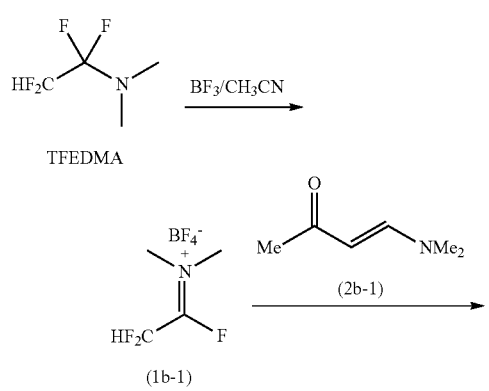

-continued

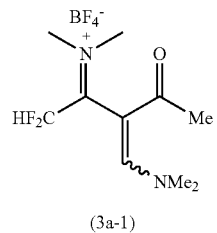

(3a-1)

19% BF$_3$-acetonitrile solution (38.9 g, 108.6 mmol) was ice-cooled under nitrogen atmosphere, and TFEDMA (16.2 g, 110.2 mmol) was slowly added thereto. Hexafluorobenzene (1.1 g, 5.7 mmol) was added thereto as an internal standard for $^{19}$F NMR, and the mixture was allowed to warm to room temperature (25° C.), and stirred at room temperature (25° C.) for 1 hr. The reaction mixture was ice-cooled, and a solution of compound (2b-1) (12.3 g, 109.7 mmol) in dehydration acetonitrile (16 ml) was slowly added thereto. After the completion of addition of compound (2b-1), the mixture was allowed to warm to room temperature (25° C.), and stirred for 2 hr. It was confirmed that vinamidinium salt (3a-1) was produced in the yield of 83% by analysis of the reaction mixture using $^{19}$F NMR. A part (20.0 g) of the reaction mixture (80.0 g) was evaporated under reduced pressure to give a brown oil (9.3 g).

$^{19}$F NMR (acetonitrile) δ=−119.0 (d, 2F).

Example 6

Synthesis of Compound (5-1) by Reaction of Vinamidinium Vinamidinium Salt with Methylhydrazine.

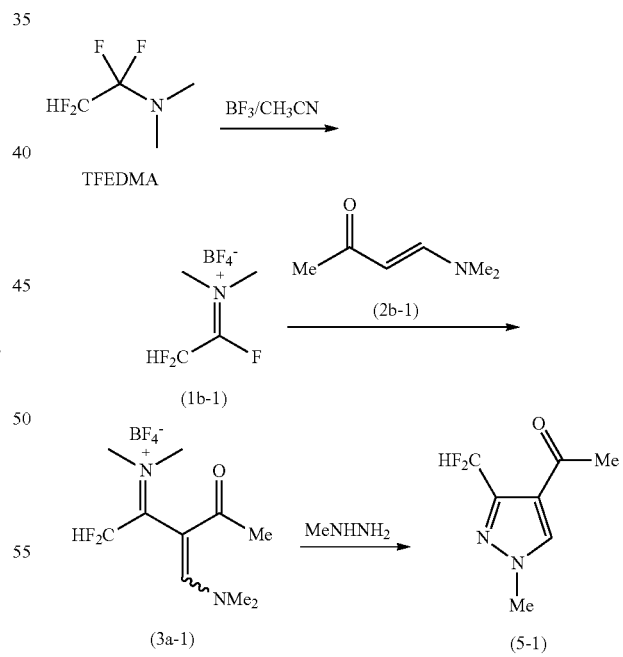

19% BF$_3$-acetonitrile solution (9.3 g, 27.3 mmol) was ice-cooled under nitrogen atmosphere, and TFEDMA (4.0 g, 27.28 mmol) was slowly added thereto. The mixture was allowed to warm to room temperature (25° C.), and stirred at room temperature (25° C.) for 1 hr. The reaction mixture was ice-cooled, and compound (2b-1) (3.1 g, 27.4 mmol) was slowly added thereto. After the completion of addition of compound (2b-1), the mixture was allowed to warm to room temperature (25° C.), stirred for 3 hr, and ice-cooled, and a solution of methylhydrazine (1.5 g, 32.6 mmol) in acetonitrile (3 ml) was slowly added thereto. The mixture was allowed to warm to room temperature (25° C.), stirred for 64 hr, and ice-cooled. The reaction was quenched with saturated aqueous sodium bicarbonate solution (10 ml), and the mixture was separated. The aqueous phase was extracted twice with ethyl acetate (5 ml), and the organic phases were combined, washed with saturated brine (10 ml), and dried over sodium sulfate, and the solvent was evaporated under reduced pressure. The obtained crude product was purified by column chromatography (developing solvent: hexane, ethyl acetate) to give compound (5-1) in the yield of 21%.

Compound (5-1)

$^1$H NMR (deuterated acetone)

δ=2.41 (s, 3H), 3.99 (s, 3H), 7.17 (t, 1H), 8.41 (s, 1H).

$^{19}$F NMR (deuterated acetone) δ=−113.8 (d, 2F).

Example 7

Synthesis of Compound (3b-1) by Hydrolysis of Vinamidinium Salt (3a-1)

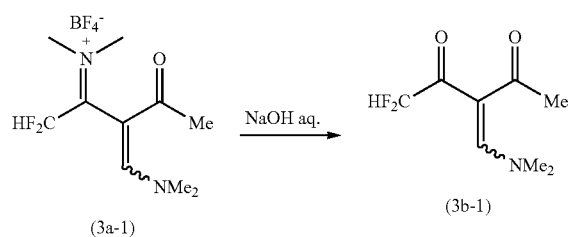

Vinamidinium salt (3a-1) (9.3 g, the amount by quantitative analysis: 22.8 mmol, obtained in Example 4) was dissolved in dehydration methylene chloride (20 ml) under nitrogen atmosphere, and the solution was ice-cooled. 10% Aqueous sodium hydroxide solution (11.0 g, 27.5 mmol) was slowly added thereto, and the mixture was stirred for 1 hr under ice-cooling, and separated. The aqueous phase was extracted twice with methylene chloride (10 ml). The organic phases were combined, washed with saturated brine (20 ml), and dried over sodium sulfate, and the solvent was evaporated under reduced pressure. The obtained crude product was purified by column chromatography (developing solvent: hexane, ethyl acetate, methanol) to give compound (3b-1) in the yield of 66%.

$^1$H NMR (CD$_3$OD) δ=2.28 (s, 3H), 2.80 (s, 3H), 3.30 (S, 3H), 6.49 (t, 1H), 8.04 (s, 1H).

$^{19}$F NMR (CD$_3$OD) δ=−123.6 (d, 2F).

Example 8

Synthesis of Compound (3b-1)

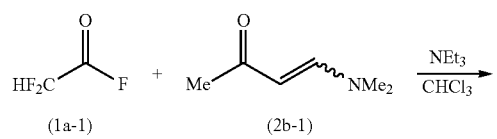

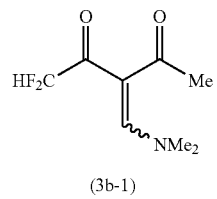

Compound (2b-1) (316 g, 2793 mmol), triethylamine (base, 203 g, 2009 mmol) and chloroform (solvent, 948 ml) were put into a reactor under nitrogen atmosphere, and difluoroacetyl fluoride (1a-1) (278 g, 2840 mmol) was added thereto with stirring while the internal temperature was kept at 0° C. The internal temperature was kept at −5° C.-+5° C. with stirring for min. It was confirmed that compound (3b-1) was produced in the yield of 100% based on compound (2b-1) by analysis of the reaction mixture by NMR.

Examples 9 to 17

Synthesis of Compound (3b-1)

The reaction was performed under the same condition as in Example 8, except that the kind and ratio of the solvent and the reaction temperature were changed. The conditions and results are collectively shown in Table 1.

TABLE 1

| Example | Solvent kind | ratio (*1) | Reaction temperature [° C.] | Yield [%] |
|---|---|---|---|---|
| 8 | CHCl$_3$ | 3 | 0 | 100 |
| 9 | CH$_2$Cl$_2$ | 3 | 0 | 99 |
| 10 | AcOEt | 3 | 0 | 92 |
| 11 | PhCl | 3 | 0 | 90 |
| 12 | none (*2) | — | 0 | 96 |
| 13 | CHCl$_3$ | 3 | 0 | 97 |
| 14 | CHCl$_3$ | 5 | 0 | 100 |
| 15 | CHCl$_3$ | 1.5 | 0 | 100 |
| 16 | CHCl$_3$ | 3 | −20 | 100 |
| 17 | CHCl$_3$ | 3 | 40 | 100 |

In Table 1, (*1) means the ratio (ml/g) of the solvent volume to the compound (2b-1) amount, and (*2) means that 1.4 mol of triethylamine was used as a base and a solvent per 1 mol of compound (1a-1). In Table 1, AcOEt is ethyl acetate, and PhCl is monochlorobenzene.

Example 18

Synthesis of Compound (5-1)

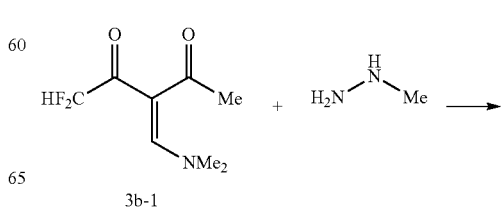

-continued

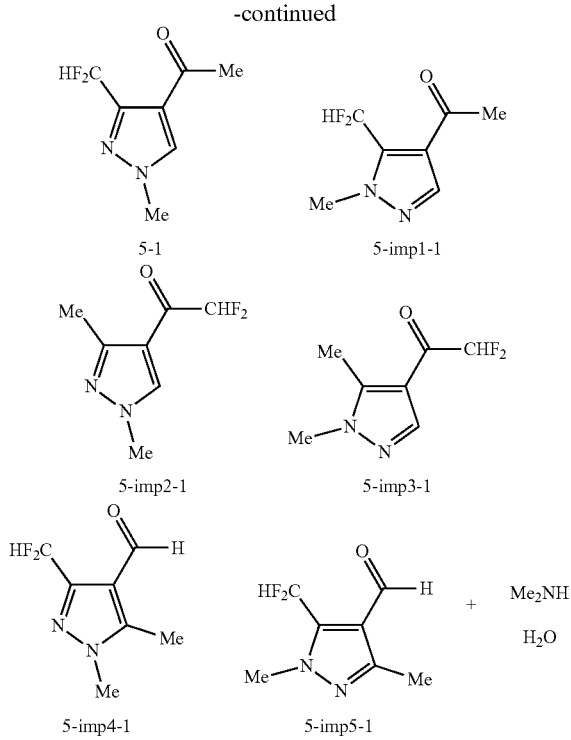

To a mixture of methylhydrazine (26.4 g, 575 mmol) and 50% aqueous dimethylamine solution (additive, 94 g, 1046 mmol) was added chloroform (solvent, 250 ml) under nitrogen atmosphere, and the mixture was cooled to −40° C. The chloroform solution (410 g) containing compound (3b-1) (100 g, 523 mmol) and triethylamine hydrofluoride, which was the reaction mixture obtained in Example 8, was slowly added dropwise thereto, and the mixture was stirred at −40° C. for 1 hr. The mixture was warmed from 0° C. to 10° C., water (260 ml) was added thereto, and the mixture was separated. It was confirmed that compound (5-1) was produced in the yield of 93%, and that compound (5-imp1-1) was produced in the yield of 1.4%, and compound (5-imp2-1), compound (5-imp2-2), compound (5-imp2-3), compound (5-imp2-4) and compound (5-imp2-5) were produced in an trace amount (less than 1%), which are by-products of cyclization, based on compound (3b-1) by quantitative analysis of the organic phase using HPLC.

Examples 19 to 26

Synthesis of Compound (5-1)

The reaction was performed under the same condition as in Example 18, except that the kind of the solvent, the kind and amount of the additive, and the reaction temperature were changed. The conditions and results are collectively shown in Table 2.

TABLE 2

| Example | Solvent kind | Reaction temperature [° C.] | Additive kind | ratio (*3) | Yield [%] |
|---|---|---|---|---|---|
| 18 | CHCl$_3$ | −40 | Me$_2$NH | 2.0 | 93 |
| 19 | CH$_2$Cl$_2$ | −20 | none | — | 54 |
| 20 | CH$_2$Cl$_2$ | −20 | Me$_2$NH | 1.0 | 76 |

TABLE 2-continued

| Example | Solvent kind | Reaction temperature [° C.] | Additive kind | ratio (*3) | Yield [%] |
|---|---|---|---|---|---|
| 21 | CH$_2$Cl$_2$ | −20 | Me$_2$NH | 2.0 | 91 |
| 22 | CH$_2$Cl$_2$ | −20 | Me$_2$NH | 2.0 | 78 |
| 23 | CH$_2$Cl$_2$ | −20 | NH$_3$ | 2.0 | 77 |
| 24 | CHCl$_3$ | −20 | Me$_2$NH | 2.0 | 86 |
| 25 | CHCl$_3$ | −30 | Me$_2$NH | 2.0 | 89 |
| 26 | CHCl$_3$ | −20 | Me$_2$NH | 3.0 | 86 |

In Table 2, (*3) means the ratio (mol/mol) of the additive amount to the compound (3b-1) amount.

Example 27

Crystallization of Compound (5-1)

The solvent of the organic phase (obtained in Example 18) of compound (5-1) was evaporated under reduced pressure, and 5-fold volume of water relative to compound (5-1) was added thereto as a crystallization solvent. The mixture was warmed to 80° C., and cooled to 0° C., and thereby, crystallization was performed. The solid of the precipitated compound (5-1) was collected, and dried to give compound (5-1) with the purity of 98.2% (HPLC area normalization) in the crystallization yield of 92%.

Examples 28 to 32

Crystallization of Compound (5-1)

The crystallization was performed under the same condition as in Example 27, except that the kind of the crystallization solvent was changed. The conditions and results are collectively shown in Table 3.

TABLE 3

| Example | Solvent | Purity | Yield |
|---|---|---|---|
| 27 | water | 98.2 | 92 |
| 28 | heptane | 96.6 | 98 |
| 29 | ethylcyclohexane | 98.6 | 98 |
| 30 | heptane/toluene | 99.0 | 99 |
| 31 | heptane/ethyl acetate | 96.6 | 96 |
| 32 | methylcyclohexane/CHCl$_3$ | 98.8 | 98 |

In Table 3, heptane/toluene is a mixed solvent by mixing heptane and toluene in the ratio of 9:1 (in this order, volume ratio), heptane/ethyl acetate is a mixed solvent by mixing heptane and ethyl acetate in the ratio of 9:1 (in this order, volume ratio), and methylcyclohexane/CHCl$_3$ is a mixed solvent by mixing methylcyclohexane and CHCl$_3$ in the ratio of 9:1 (in this order, volume ratio).

Example 33

Synthesis of Compound (6-1)

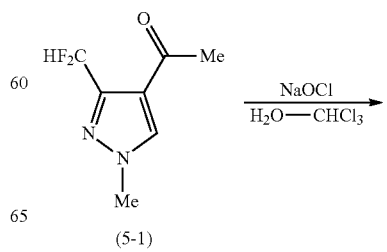

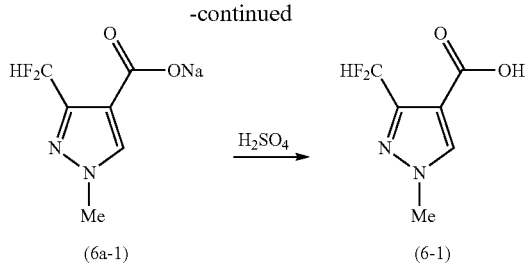

(6a-1) → (6-1)

Compound (6-1) (phase-transfer catalyst, 10.2 g, 57 mmol), sodium hydroxide (2.7 g, 68 mmol) and water (200 g) were put successively into a reactor under air atmosphere, the mixture was dissolved, and 13.75% aqueous sodium hypochlorite solution (1016 g, 1877 mmol) was added thereto. A solution prepared by dissolving compound (5-1) (100 g, 569 mmol, obtained in the same manner as in Example 18) in chloroform (solvent, 450 g, 300 ml) was added dropwise thereto with stirring over 1 hr, while the internal temperature was kept at 20° C.-30° C., and thereby, the reaction was performed.

By analysis of the reaction mixture 1 hr after the completion of the addition dropwise using NMR and HPLC, the disappearance of compound (5-1) and the production of compound (6a-1) were confirmed. The reaction mixture was separated, and to the recovered aqueous phase was added 10% aqueous sodium sulfite solution (289 g, 229 mmol) while the temperature was kept at 30° C. or below.

Then, after confirming that the sodium hypochlorite did not remain by potential measurement and iodine starch reaction, conc. sulfuric acid (114 g, 1137 mmol) was added thereto while the internal temperature was kept at 30° C. or below. When the pH of the solution became 4 or less, white solid was precipitated, and the pH of the solution finally became 1. The precipitated solid was collected by filtration, washed with water, and dried. It was confirmed that the dried solid was compound (6-1) with the purity of 99.9% (HPLC area normalization) in the yield of 97% (based on the total amount of compound (5-1) and compound (6-1) added as a phase-transfer catalyst) by HPLC analysis.

Examples 34 to 37

Synthesis of Compound (6-1)

The reaction was performed under the same condition as in Example 33, except that the amount of phase-transfer catalyst and the reaction temperature were changed. The conditions and results are collectively shown in Table 4.

TABLE 4

| | Solvent | | Temperature | Phase-transfer catalyst | | Reaction | | |
|---|---|---|---|---|---|---|---|---|
| Ex. | kind | ratio (*4) | [° C.] | kind | ratio (*5) | time [hr] | yield [%] | purity [%] |
| 33 | CHCl$_3$ | 3 | 30 | compound (6-1) | 0.1 | 2 | 97 | 99.9 |
| 34 | CHCl$_3$ | 3 | 50 | none | — | 1 | 87 | 99.9 |
| 35 | CHCl$_3$ | 3 | 10 | compound (6-1) | 0.1 | 18 | 92 | 99.9 |
| 36 | CHCl$_3$ | 1 | 30 | none | — | 2 | 93 | 99.9 |

TABLE 4-continued

| | Solvent | | Temperature | Phase-transfer catalyst | | Reaction | | |
|---|---|---|---|---|---|---|---|---|
| Ex. | kind | ratio (*4) | [° C.] | kind | ratio (*5) | time [hr] | yield [%] | purity [%] |
| 37 | CHCl$_3$ | 3 | 30 | compound (6-1) | 0.2 | 3 | 94 | 99.9 |

In Table 4, (*4) means the ratio (ml/g) of the organic solvent volume to the compound (5-1) amount, and (*5) means the ratio (mol/mol) of the phase-transfer catalyst amount to the compound (5-1) amount.

Example 38

Synthesis of Compound (6-1)

Compound (5-1) (38 g, 218 mmol, obtained in the same manner as in Example 18), compound (6-1) (phase-transfer catalyst, 3.9 g, 22.2 mmol) and sodium hydroxide (1.1 g, 27.5 mmol) were suspended in water (80 g) in a reactor under air atmosphere, and 14.5% aqueous sodium hypochlorite solution (364 g, 709 mmol) was added to the reactor, while the internal temperature was kept at 20° C.-30° C.

By analysis of the reaction mixture 2 hr after the completion of the addition dropwise using NMR and HPLC, the disappearance of compound (5-1) and the production of compound (6a-1) were confirmed. The reaction mixture was separated, and to the recovered aqueous phase was added 10% aqueous sodium sulfite solution (111 g). After confirming that the sodium hypochlorite did not remain by potential measurement and iodine test paper, to the aqueous phase was added conc. sulfuric acid (44 g). When the pH of the solution became 3 or less, white solid was precipitated. The precipitated solid was collected by filtration, washed with water, and dried. It was confirmed that the dried solid was compound (6-1) with the purity of 99.5% (HPLC area normalization) in the yield of 97% (based as in Example 33) by HPLC analysis.

Example 39

Synthesis of Compound (6-1)

Compound (5-1) (40 g, 230 mmol, obtained in the same manner as in Example 18), compound (6-1) (phase-transfer catalyst, 4.0 g, 22.7 mmol) and sodium hydroxide (1.1 g, 27.5 mmol) were suspended in water (80 g) in a reactor under air atmosphere, and 14.5% aqueous sodium hypochlorite solution (372 g, 700 mmol) was added to the reactor, while the internal temperature was kept at 5° C.-15° C.

By analysis of the reaction mixture 2 hr after the completion of the addition dropwise using NMR and HPLC, the disappearance of compound (5-1) and the production of compound (6a-1) were confirmed. The reaction mixture was separated, and to the recovered aqueous phase was added 10% aqueous sodium sulfite solution (111 g). After confirming that the sodium hypochlorite did not remain by potential measurement and iodine test paper, to the aqueous phase was added conc. sulfuric acid (44 g). When the pH of the solution became 3 or less, white solid was precipitated. The precipitated solid was collected by filtration, washed with water, and dried. It was confirmed that the dried solid was compound (6-1) with the purity of 99.9% (HPLC area normalization) in the yield of 97% (based as in Example 33) by HPLC analysis.

INDUSTRIAL APPLICABILITY

According to the production method of the present invention, pyrazole derivatives useful as intermediates for medicines or agrichemicals can be produced by an industrially advantageous and economically excellent method.

This application is based on patent application No. 2015-65271 filed on Mar. 26, 2015 and No. 2015-111722 filed on Jun. 1, 2015 in Japan, the contents of which are encompassed in full herein.

The invention claimed is:

1. A compound represented by formula (5a)

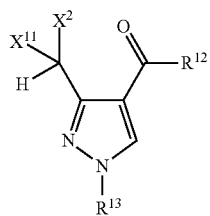
(5a)

wherein
  $R^{12}$ is a methyl group or an ethyl group,
  $R^{13}$ is a hydrogen atom, a methyl group or an ethyl group, and
  $X^{11}$ and $X^{12}$ are each independently a fluorine atom or a chlorine atom.

2. A method of producing a compound represented by formula (5)

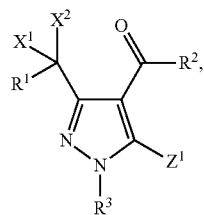
(5)

which comprises
  reacting a compound represented by formula (1)

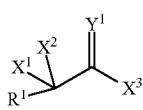
(1)

with a compound represented by formula (2)

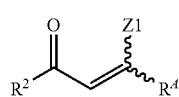
(2)

to obtain a compound represented by formula (3)

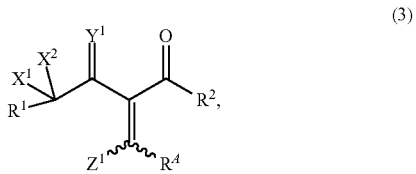
(3)

and
  reacting the compound represented by the formula (3) with a compound represented by formula (4a)

$$R^3\text{—}NHNH_2 \quad (4a)$$

to obtain a compound represented by formula (5),
wherein
  $R^1$ is a hydrogen atom or a halogen atom,
  $R^2$ is a $C_{1-8}$ alkyl group,
  $R^3$ is a hydrogen atom or a $C_{1-8}$ alkyl group,
  $X^1$ and $X^2$ are each independently a fluorine atom or a chlorine atom,
  $Z^1$ is a hydrogen atom or a $C_{1-8}$ alkyl group,
  $R^4$ is $NR^5R^6$, and $R^5$ and $R^6$ are each independently a $C_{1-8}$ alkyl group,
  $Y^1$ is an oxygen atom,
  $X^3$ is a halogen atom, and
  the wavy lines mean that the configuration of $Z^1$ and $R^4$ relating to the double bond is E or Z.

3. A method of producing a compound represented by formula (5-1)

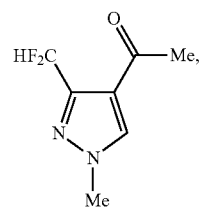
(5-1)

which comprises
  reacting 1,1,2,2-tetrafluoro-N,N-dimethylethanamine with $BF_3$ to obtain a compound represented by formula (1b-1)

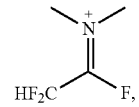
(1b-1)

reacting the compound represented by formula (1b-1) with a compound represented by formula (2b-1)

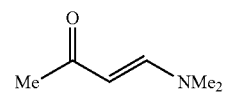
(2b-1)

to obtain a compound represented by formula (3a-1)

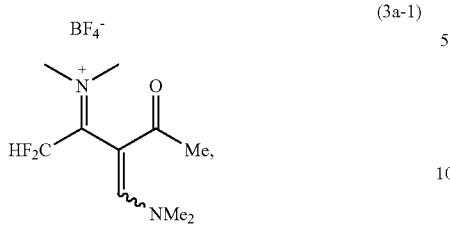
(3a-1)

and reacting the compound represented by formula (3a-1) with methylhydrazine to obtain a compound represented by (5-1).

4. A method of producing a pyrazole derivative represented by formula (6)

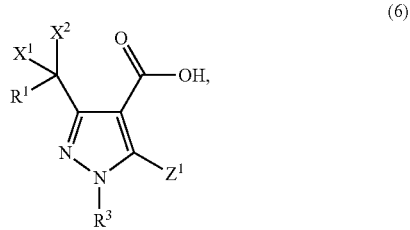
(6)

which comprises reacting a compound represented by formula (5)

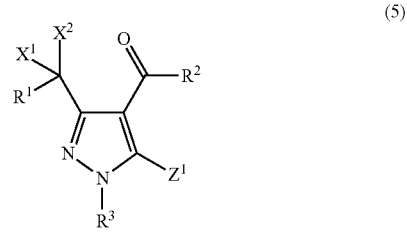
(5)

with an oxidant
wherein
$R^1$ is a hydrogen atom or a halogen atom,
$R^2$ is a $C_{1-8}$ alkyl group,
$R^3$ is a hydrogen atom or a $C_{1-8}$ alkyl group,
$X^1$ and $X^2$ are each independently a fluorine atom or a chlorine atom, and
$Z^1$ is a hydrogen atom or a $C_{1-8}$ alkyl group.

5. The compound of claim 1, wherein $R^{12}$ is a methyl group.

6. The compound of claim 1, wherein $R^{13}$ is a methyl group.

7. The compound of claim 1, wherein each of $R^{12}$ and $R^{13}$ is a methyl group.

8. The compound of claim 1, wherein each of $X^{11}$ and $X^{12}$ is a fluorine atom.

9. The compound of claim 1, wherein each of $X^{11}$ and $X^{12}$ is a chlorine atom.

10. The compound of claim 1, wherein each of $X^{11}$ and $X^{12}$ is a fluorine atom, and each of $R^{12}$ and $R^{13}$ is a methyl group.

11. The compound of claim 1, wherein $R^{12}$ is an ethyl group.

12. The compound of claim 1, wherein $R^{13}$ is an ethyl group.

13. The compound of claim 1, wherein each of $R^{12}$ and $R^{13}$ is an ethyl group.

14. The compound of claim 1, wherein $R^{13}$ is a hydrogen atom.

15. The compound of claim 1, wherein $R^{12}$ is a methyl group, and $R^{13}$ is a hydrogen atom.

16. The compound of claim 1, wherein $R^{12}$ is an ethyl group, and $R^{13}$ is a hydrogen atom.

17. The compound of claim 1, wherein $R^{12}$ is a methyl group, and $R^{13}$ is an ethyl group.

18. The compound of claim 1, wherein $R^{12}$ is an ethyl group, and $R^{13}$ is a methyl group.

19. The compound of claim 1, wherein (a) $R^{12}$ is a methyl group, (b) $R^{13}$ is an ethyl group, and (c) both $X^{11}$ and $X^{12}$ are fluorine atoms or both $X^{11}$ and $X^{12}$ are chlorine atoms.

20. The compound of claim 1, wherein (a) $R^{12}$ is an ethyl group, (b) $R^{13}$ is a methyl group, and (c) both $X^{11}$ and $X^{12}$ are fluorine atoms or both $X^{11}$ and $X^{12}$ are chlorine atoms.

* * * * *

UNITED STATES PATENT AND TRADEMARK OFFICE
CERTIFICATE OF CORRECTION

PATENT NO. : 10,239,841 B2
APPLICATION NO. : 15/560934
DATED : March 26, 2019
INVENTOR(S) : Ishibashi et al.

Page 1 of 1

It is certified that error appears in the above-identified patent and that said Letters Patent is hereby corrected as shown below:

In the Claims

Claim 1, Column 47, Lines 15-25, formula (5a) should read as follows:

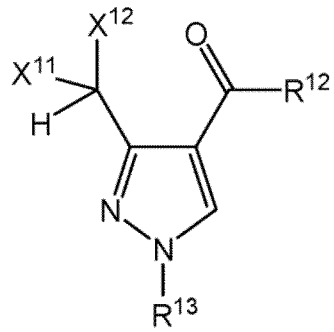

(5a)

Signed and Sealed this
Thirtieth Day of July, 2019

Andrei Iancu
*Director of the United States Patent and Trademark Office*